(12) United States Patent
Zhao

(10) Patent No.: US 9,069,185 B2
(45) Date of Patent: Jun. 30, 2015

(54) HIGH EFFICIENCY OPTIC

(71) Applicant: Abbott Medical Optics Inc., Santa Ana, CA (US)

(72) Inventor: Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 49 days.

(21) Appl. No.: 13/934,575

(22) Filed: Jul. 3, 2013

(65) Prior Publication Data

US 2014/0009736 A1    Jan. 9, 2014

Related U.S. Application Data

(60) Provisional application No. 61/667,544, filed on Jul. 3, 2012.

(51) Int. Cl.
| | |
|---|---|
| *G02C 7/04* | (2006.01) |
| *G02C 7/06* | (2006.01) |
| *G02C 7/02* | (2006.01) |
| *A61F 2/16* | (2006.01) |

(52) U.S. Cl.
CPC ........ *G02C 7/022* (2013.01); *G02C 7/06* (2013.01); *G02C 7/024* (2013.01); *A61F 2/1654* (2013.01); *G02C 7/028* (2013.01); *G02C 7/041* (2013.01); *G02C 2202/20* (2013.01)

(58) Field of Classification Search
CPC ......... G02C 7/022; G02C 7/046; G02C 7/049
USPC ............. 351/159.11, 159.15, 159.26, 159.35, 351/159.44
See application file for complete search history.

(56) References Cited

U.S. PATENT DOCUMENTS

| | | | |
|---|---|---|---|
| 4,856,234 | A | 8/1989 | Goins |
| 5,322,649 | A | 6/1994 | Rheinish et al. |
| 5,699,142 | A | 12/1997 | Lee et al. |

(Continued)

FOREIGN PATENT DOCUMENTS

| | | |
|---|---|---|
| EP | 351471 A2 | 1/1990 |
| WO | 2006023404 A2 | 3/2006 |
| WO | 2010071751 A1 | 6/2010 |

OTHER PUBLICATIONS

International Search Report and Written Opinion for Application No. PCT/US2013/049227, mailed on Sep. 10, 2013, 13 pages.

*Primary Examiner* — Darryl J Collins
(74) *Attorney, Agent, or Firm* — Abbott Medical Optics Inc.

(57) ABSTRACT

Ophthalmic lenses and methods for their design and use involve displacement functions based on the sum of a continuous cosine function and a continuous sine function, optionally over a plurality of echelettes. Exemplary monofocal and multifocal diffractive ophthalmic lenses provide reduced light scatter and/or improved light energy distribution properties. Such properties can be provided by diffractive profiles, often having subtlety shaped echelettes with appropriately curving profiles. Light scatter may be generated by the sharp corners associated with vertical steps between adjacent conventional diffractive echelettes. Smooth diffractive profiles of the invention reduce light scatter. Light energy directed toward non-viewing diffractive orders may have a unwanted effects on vision quality. Diffractive profiles as described herein may limit the light energy in certain, selected orders, thereby improving viewing quality and mitigating unwanted effects such as dysphotopsia. Diffractive profiles may also vary the light energy distributed between individual echelettes, providing additional advantages in various viewing situations.

57 Claims, 13 Drawing Sheets

(56) References Cited

U.S. PATENT DOCUMENTS

| | | | |
|---|---|---|---|
| 5,888,122 A | 3/1999 | Gupta et al. | |
| 6,830,332 B2 | 12/2004 | Piers et al. | |
| 2002/0082690 A1 | 6/2002 | Sarbadhikari | |
| 2008/0273167 A1* | 11/2008 | Clarke | 351/159 |
| 2009/0268155 A1 | 10/2009 | Weeber | |

* cited by examiner $$\Delta(\rho) := \Delta_0 \cdot \left[\left[1 - \left(\frac{\rho}{r_1}\right)^n\right] \cdot \left[1 - \left(\frac{\rho}{r_1}\right)^n\right] - \left[\left(\frac{\rho}{r_1}\right)^n\right]\right] \cdot \left[0.5 - 0.5\cos\left[\pi \cdot \frac{\rho^2}{q_1^2}\left[1.0 + \left(\rho - q_1^2\right)\right]\right]\right] \cdot \left[Y\_min + (Y\_max - Y\_min) \cdot \left[0.5 \tanh\left[\frac{(\rho - X\_shift)}{m}\right] + 0.5\right]\right]$$

FIG. 4E $$\Delta(\rho) :=$$

$$\Delta\_1(\rho) \cdot \left[ 1 - \left[ \text{Ymin} + (\text{Ymax} - \text{Ymin}) \cdot \left( C_3 + C_4 \cdot \tanh\left( \frac{\sqrt{\rho} - X\_shift}{\text{Width}} \right) + w \right) \right] \right]$$

$$+$$

$$\Delta\_2(\rho) \cdot \left[ \text{Ymin} + (\text{Ymax} - \text{Ymin}) \cdot \left( C_3 + C_4 \cdot \tanh\left( \frac{\sqrt{\rho} - X\_shift}{\text{Width}} \right) + w \right) \right]$$

FIG. 4F

HIGH EFFICIENCY OPTIC

CROSS-REFERENCES TO RELATED APPLICATIONS

This application claims priority to U.S. Application No. 61/667,544, filed on Jul. 3, 2012. This application is related to U.S. Pat. No. 7,871,162, U.S. Patent Publication Nos. 2009/0268155 and 2011/0109875, and U.S. patent application Ser. No. 12/962,255 filed Dec. 7, 2010. The entire content of each of these filings is incorporated herein by reference for all purposes. Full Paris Convention priority is hereby expressly reserved.

BACKGROUND OF THE INVENTION

Embodiments of the present invention relate to ophthalmic lenses such as, for example, contact lenses or intraocular lenses (IOLs). Exemplary embodiments include monofocal and multifocal diffractive ophthalmic lenses having reduced light scatter and/or improved light energy distribution, for example, through subtle shaping of echelettes with appropriately curving profiles.

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of cataracts. Cataracts may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intra-ocular lens or "IOL".

A variety of technologies have been developed to enhance the ability of IOLs to facilitate viewing. Multifocal IOLs may, for example, often rely on a diffractive optical surface to direct portions of the light energy toward differing focal distances, thereby allowing the patient to clearly see both near and far objects. Alternative diffractive multifocal ophthalmic lenses (including contact lenses or the like) have been proposed for treatments of presbyopia without removal of the natural crystalline lens. Diffractive optical surfaces, either monofocal or multifocal, may also be configured to provide reduced chromatic aberrations.

Like other lenses, diffractive monofocal or multifocal lenses can make use of a material having a given refractive index and a surface curvature to provide a refractive power. Diffractive lenses also have a diffractive profile which confers the lens with a diffractive power that contributes to the overall optical power of the lens. The diffractive profile is typically characterized by a number of diffractive zones. The diffractive power is related to the properties of these zones, for instance their number, shape, size and position. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes a diameter and a shape or slope of the optical zone, as well as a height or step height of the transition zone. The diameters of the echelettes largely determine the power(s) of the lens and the step height of the transition zones largely determines the light distribution between the different add powers. Together, these echelettes form a diffractive profile, often saw-toothed or stepped, on one of the surfaces of the lens.

A multifocal diffractive profile of the lens can be used to mitigate presbyopia by providing two or more optical powers, for example, one for near vision and one for far vision. These lenses may be in the form of a multifocal contact lens, most commonly a bifocal contact lens. The lenses may also take the form of an intraocular lens placed within the capsular bag of the eye, replacing the original lens.

Although monofocal and multifocal diffractive ophthalmic lenses have greatly improved the quality of vision for many patients, additional improvements would still be beneficial. For example, some pseudophakic patients may experience scatter effects, such as halos. Therefore, monofocal and multifocal diffractive multifocal lenses having diffractive profiles resulting in reduced scatter (and thus an improved quality of vision) may be beneficial. For multifocal lenses, along with directing portions of the incident light energy at focal distances suitable for near and far viewing, diffractive optics may also direct significant light energy at other non-viewing foci, which can contribute to unwanted light-related visual phenomenon experienced by the patient (dysphotopsia). Having non-viewing foci of diffractive optics of multifocal lenses cannot be completely avoided. However, diffractive multifocal lenses having diffractive profiles which optimize the light energy distribution between viewing and non-viewing foci to improve quality of vision would also be beneficial. Controllably varying light distributions over the diffractive profile may also provide some advantages, so that diffractive multifocal lenses having diffractive profiles which vary light distribution over the profile may be desirable.

BRIEF SUMMARY OF THE INVENTION

The present invention generally provides improved lenses and imaging techniques. Embodiments of the present invention provide improved ophthalmic lenses (including, for example contact lenses, intraocular lenses (IOLs), and the like) and associated methods for their design and use. Exemplary embodiments provide monofocal and/or multifocal diffractive ophthalmic lenses having reduced light scatter and/or improved light energy distribution, for example, through subtle shaping of echelettes with appropriately curving profiles extending between the optical zones of adjacent echelette surfaces. In some embodiments, diffractive ophthalmic lenses having multiple foci often use a zero order diffraction for far vision and a first order diffraction for near vision, while limiting the light energy directed to the other unwanted orders. Specifically, it has been recognized that light energy directed to foci of a selected subset of the non-viewing orders—those that are closest to the zero order focus—can have an disproportionate effect on vision quality. By limiting the light energy in such selected orders (optionally, even at the cost of directing more total light energy to higher and/or non-viewing order foci), dysphotopsia may be mitigated. Imposing a controlled curvature across a series of echelettes can be used to tailor energies of the various foci or diffraction orders so as to provide such benefits, and/or may be used to limit scatter effects which may otherwise be generated by the sharp corners associated with vertical steps between adjacent conventional diffractive echelettes.

In a first aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated step heights that are substantially equal to one another. The diffractive profile has, in the visible waveband, a zeroth diffractive order and a first diffractive order having a diffraction add power. The zeroth and first diffraction orders have diffraction efficiencies which change with radius from the optical axis.

In many embodiments, the diffractive profile is characterized by a continuous function over a plurality of echelettes.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The zeroth and the first diffraction orders have diffraction efficiencies which change depending on the number of surrounding echelettes.

In another aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated step heights that are substantially equal to one another. The diffractive profile has, in the visible waveband, a first diffractive order and a second diffractive order having a diffraction add power. The first and second diffraction orders have diffraction efficiencies which change with radius from the optical axis.

In many embodiments, the diffractive profile is characterized by a continuous function over a plurality of echelettes.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The first and the second diffraction orders have diffraction efficiencies which change depending on the number of surrounding echelettes.

In another aspect, the invention provides a method for viewing with a diffractive ophthalmic lens using an eye of a patient. The ophthalmic lens includes a plurality of echelettes with associated step heights that are substantially equal to one another. The echelettes each have a characteristic profile and define a diffractive surface. The diffractive surface has in the visible waveband, a zeroth diffractive order and a first diffractive order. The method comprises changing the diffractive efficiency of the first diffractive order of the echelettes with radius from the optical axis.

In many embodiments, changing the diffractive efficiency of the first diffractive order of each of the echelettes with radius from the optical axis comprises changing the profile of each of the echelettes with radius from the optical axis.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The zeroth and the first diffraction orders have diffraction efficiencies which change depending on the number of surrounding echelettes.

In many embodiments, any one of the step heights do not vary by more than 20 percent from an average of all the step heights.

In one aspect, embodiments of the present invention encompass ophthalmic lenses, and methods of their use and manufacture. Exemplary lenses include an anterior face with an anterior refractive profile and a posterior face with a posterior refractive profile, where the faces disposed about an optical axis. Lenses also include a diffractive profile imposed on one of the refractive profiles. The diffractive profile includes a plurality of echelettes, and the diffractive profile is characterized by a displacement function over the plurality of echelettes. The displacement function includes the sum of a continuous cosine function and a continuous sine function over the plurality of echelettes. In some instances, the continuous sine function is affected by a hyperbolic tangent function. In some instances, the continuous cosine function is affected by a hyperbolic tangent function. In some instances, the continuous sine function is affected by a first hyperbolic tangent function, and the continuous cosine function is affected by a second hyperbolic tangent function. In some instances, the sum of the first and second hyperbolic tangent functions is equal to one. In some instances, the plurality of echelettes diffracts at least about 95% to a first diffractive order. In some instances, the diffractive profile distributes light energy to the 0th and 1st diffractive orders in an amount that is greater than 95%. In some instances, the diffractive profile provides a light scatter characteristic that scatters less than 5% of light. According to some embodiments, the displacement function corresponds to a displacement from a reference plane perpendicular to the optical axis. Optionally, the lens may be a multifocal lens. In some instances, the lens may be a monofocal lens.

In another aspect, embodiments of the present invention encompass methods for treating an eye of a person. Exemplary methods include administering a diffractive ophthalmic lens to the eye of the person, where the ophthalmic lens includes an anterior face with an anterior refractive profile and a posterior face with a posterior refractive profile. The faces may be disposed about an optical axis. The lens may also include a diffractive profile imposed on one of the refractive profiles. The diffractive profile may include a plurality of echelettes. The diffractive profile may be characterized by a displacement function over the plurality of echelettes. The displacement function may include the sum of a continuous cosine function and a continuous sine function over the plurality of echelettes. In some instances, the continuous sine function is affected by a hyperbolic tangent function. In some instances, the continuous cosine function is affected by a hyperbolic tangent function. In some instances, the continuous sine function is affected by a first hyperbolic tangent function, and the continuous cosine function is affected by a second hyperbolic tangent function. In some instances, the sum of the first and second hyperbolic tangent functions is equal to one. In some instances, the plurality of echelettes diffracts at least about 95% to a first diffractive order. In some instances, the diffractive profile distributes light energy to the 0th and 1st diffractive orders in an amount that is greater than 95%. In some instances, the diffractive profile provides a light scatter characteristic that scatters less than 5% of light. According to some embodiments, the displacement function corresponds to a displacement from a reference plane perpendicular to the optical axis. Optionally, the lens may be a multifocal lens. In some instances, the lens may be a monofocal lens.

In still another aspect, embodiments of the present invention encompass methods of manufacturing an ophthalmic lens for an eye of a person. Exemplary methods may include obtaining or receiving a lens material, and processing the lens material to produce the ophthalmic lens, so that the ophthalmic lens comprises an anterior face with an anterior refractive profile and a posterior face with a posterior refractive profile. The faces may be disposed about an optical axis. The lens may also include a diffractive profile imposed on one of the refractive profiles. The diffractive profile may include a plurality of echelettes. The diffractive profile may be characterized by a displacement function over the plurality of echelettes. The displacement function may include the sum of a continuous cosine function and a continuous sine function over the plurality of echelettes. In some instances, the continuous sine function is affected by a hyperbolic tangent function. In some instances, the continuous cosine function is affected by a hyperbolic tangent function. In some instances, the continuous sine function is affected by a first hyperbolic tangent function, and the continuous cosine function is affected by a second hyperbolic tangent function. In some instances, the sum of the first and second hyperbolic tangent functions is equal to one. In some instances, the plurality of echelettes diffracts at least about 95% to a first diffractive order. In some instances, the diffractive profile distributes light energy to the 0th and 1st diffractive orders in an amount that is greater than 95%. In some instances, the diffractive profile provides a light scatter characteristic that scatters less than 5% of light. According to some embodiments, the displacement function corresponds to a displacement from a reference plane perpendicular to the optical axis. Optionally, the lens may be a multifocal lens. In some instances, the lens may be a monofocal lens.

For a fuller understanding of the nature and advantages of the present invention, reference should be had to the ensuing detailed description taken in conjunction with the accompanying drawings.

BRIEF DESCRIPTION OF THE DRAWINGS

FIG. 4E is an equation for a formula for a diffractive profile according to an embodiment of the present invention.

FIG. 4F shows an exemplary equation for a displacement function for a lens according to embodiments of the present invention.

Figure 1A:
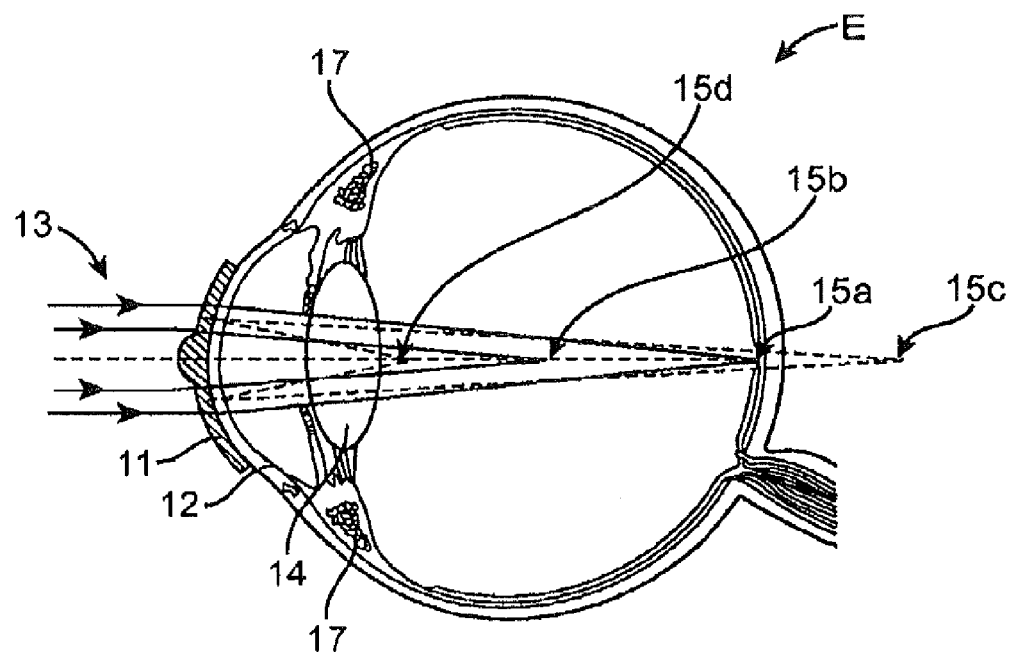
FIG. 1A is a cross-sectional view of an eye with a multifocal contact lens.

For illustration purposes, the profile geometries shown in the aforementioned figures were not drawn exactly to scale. In some cases, the heights of the diffractive profiles shown in the figures is generally in the order of about 0.5 millimeters and about 2.0 millimeters although the heights may vary depending on factors such as the amount of correction needed by the patient, the refractive index of the lens material and surrounding medium, and the desired distribution of light between wanted diffraction orders.

DETAILED DESCRIPTION OF THE INVENTION

The present invention generally provides improved lenses and imaging systems. Embodiments of the invention may find their most immediate use may be in the form of improved ophthalmic devices, systems, and methods. Exemplary embodiments of the present invention provide improved ophthalmic lenses (including, for example contact lenses, intraocular lenses (IOLs), corneal lenses and the like) and associated methods for their design and use. Embodiments of the present invention include monofocal diffractive lenses, bifocal diffractive lenses, and multifocal diffractive lenses. Exemplary embodiments provide multifocal diffractive ophthalmic lenses having reduced light scatter and/or improved light energy distribution so as to enhance viewing performance, for example, through subtle shaping of a smoothly curving profile extending across a plurality of echelettes. The surface is generally optically smooth to help reduce scatter. As used herein, "optically smooth" means having an average roughness that is much smaller than the wavelength of visible light (e.g., having an rms roughness that is less that 100 nm, $\lambda/10$, or the like, where $\lambda$ is a wavelength of light).

Diffractive ophthalmic lenses having multiple foci often use zero order diffraction for far vision and first order diffraction for near vision. Some portion of the light energy is also directed to other, non-viewing orders. As used herein, the term "non-viewing order" means a diffractive order containing energy that is not useful in forming an image on the retina of an eye. By recognizing that foci of the non-viewing orders that are closest to the zero order focus can have the largest negative effect on vision quality, and by limiting the light energy in such selected non-viewing orders, dysphotopsia (e.g., scattering or halo effects) may be mitigated, even if more total cumulative light energy ends up being directed to higher order and/or other non-viewing foci. Imposing a controlled shape or curvature across a plurality of echelettes can be used to tailor energies of the various foci so as to provide such benefits, and may also be used to limit deleterious scatter that can otherwise be generated by the sharp corners associated with vertical steps between adjacent conventional diffractive echelettes.

The shape or diffractive profile of a multifocal lens can impact the light energy distribution between foci. For example, known multifocal lenses often seek to distribute imaging light energy between 2 viewing foci: one (typically the zero order focus) corresponding with far viewing distances and one (typically the first order focus) corresponding to near viewing distances. The remaining light is distributed to other non-viewing foci. For example, a conventional multifocal lens with a desired 50%:50% light distribution between the far and near foci, may also result in about 41% of the light energy directed to the far focus, about 41% of the light energy directed to the near focus, and about 18% of the light energy being directed to non-viewing and/or higher order foci, the higher order foci being generally situated symmetrically around the 2 main viewing foci. In order of diminishing brightness, the next brightest foci may, for example, be the $-1^{st}$ and $2^{nd}$ order foci, each of which are non-viewing foci and may receive about 4.5% of the light energy.

The non-viewing and/or higher order foci have a negative effect on the quality of vision. However, the negative effect of the various non-viewing foci will not be the same, and will not depend solely on the portion of incident light energy each focus receives. Instead, higher order foci that are close to the zero order focus will tend to have a disproportionately larger negative effect on perceived scatter and halo effects. Too much light energy (and thus brightness) in such higher order foci can contribute to dysphotopsia. Therefore, diffractive multifocal lenses having diffractive profiles which optimize and/or selectively tailor the light energy distribution between the various foci may improve quality of vision and reduce dysphotopsia for pseudophakic patients, contact lens users, and the like.

The structures of the present invention may also present additional advantages by enhancing the design flexibility through selectively curving echelette profiles, with the curvatures presenting additional design variables that can be used to benefit overall viewing performance. For example, varying light distributions over the diffractive profile may also provide advantages. Reading is often done in bright light conditions in which the pupil is small. In contrast, night-time driving is done in low light conditions in which the pupil is large. It may be advantageous to vary light distribution radially across the diffractive profile so that different light energy splits are provided based on the viewing situation and resulting pupil size. In some such ophthalmic lenses, a greater proportion of light energy may be transmitted to the far focus from a peripheral portion of the lens to accommodate for low light, far viewing conditions such as night time driving, with the near viewing receiving relatively more light energy from a central portion of the diffractive profile. Varying curvature and/or shapes of the echelettes radially may thus provide diffractive multifocal lenses having a diffractive profiles which vary light distribution over the profile as the pupil changes in size.

As another example of the benefits of intentional and controlled curving diffractive profiles for ophthalmic lenses, the scatter of multifocal diffractive lenses may be higher than that of corresponding monofocal and/or purely refractive designs. The diffractive profile of multifocal diffractive lenses may play a significant role in producing such scatter, and appropriately controlled curving profiles may be employed to inhibit such scatter, often providing such benefits in combination with one or more of the other improvements described herein.

FIG. 1A is a cross-sectional view of an eye E fit with a multifocal contact lens 11. Multifocal contact lens 11 may, for example, comprise a bifocal contact lens. Multifocal contact lens 11 covers at least a portion of cornea 12 at the front of eye E and is generally centered about the optical axis of eye E.

Each major face of lens 11, including the anterior (front) surface and posterior (back) surface, generally has a refractive profile. The two surfaces together, in relation to the properties of the air, tear film, cornea, and other optical components of the overall optical system, define the effects of the lens 11 on the imaging performance by eye E. Conventional, monofocal contact lenses have a refractive power based on the refractive index of the material from which the lens is made, and also on the curvature or shape of the front and rear surfaces or faces of the lens.

In a young, healthy eye contraction and relaxation of ciliary muscles 17 surrounding the natural lens 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore need corrective optics having two optical powers, one for near vision and one for far vision, as provided by multifocal contact lens 11.

Multifocal lenses may optionally also make use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a generally higher overall power (sometimes referred to as a positive add power) suitable for viewing at near distances.

Rather than relying entirely on the refractive properties of the lens, multifocal diffractive contact lenses or IOLs can also have a diffractive power. The diffractive power can, for example, comprise positive add power, and that add power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens acts as a diffraction grating and directs incoming light into a number of diffraction orders. As light 13 enters from the front of the eye, multifocal contact lens and the natural lens 14 bend light 13 to form a far field focus 15a on retina 16 for viewing for distant objects and a near field focus 15b for objects close to the eye. Depending on the distance form the source of light 13, the focus on retina 16, the viewing focus, may be near field focus 15b instead. Far field focus 15a is associated with $0^{th}$ diffractive order and near field focus 15b is associated with the $1^{st}$ diffractive order.

Multifocal ophthalmic lens 11 typically distributes the majority of light energy into the two viewing orders, often with the goal of splitting imaging light energy evenly (50%: 50%). However, a significant portion of the incident light energy is directed into other, non-viewing diffractive orders 15c, 15d, and the like (the non-viewing orders typically comprising the $2^{nd}, 3^{rd}, \ldots, -1^{st}, -2^{nd}, -3^{rd}, \ldots$) such that the $0^{th}$ and $1^{st}$ order each receive about 40.5% of the light energy when standard ideal parabolic echelettes with sharp vertical transitions are used. The remaining percentage of the light energy is received by the higher and lower orders, with the $-1$ and $2^{nd}$ order each receiving about 4.5% of the light energy for such lenses.

Figure 1B:
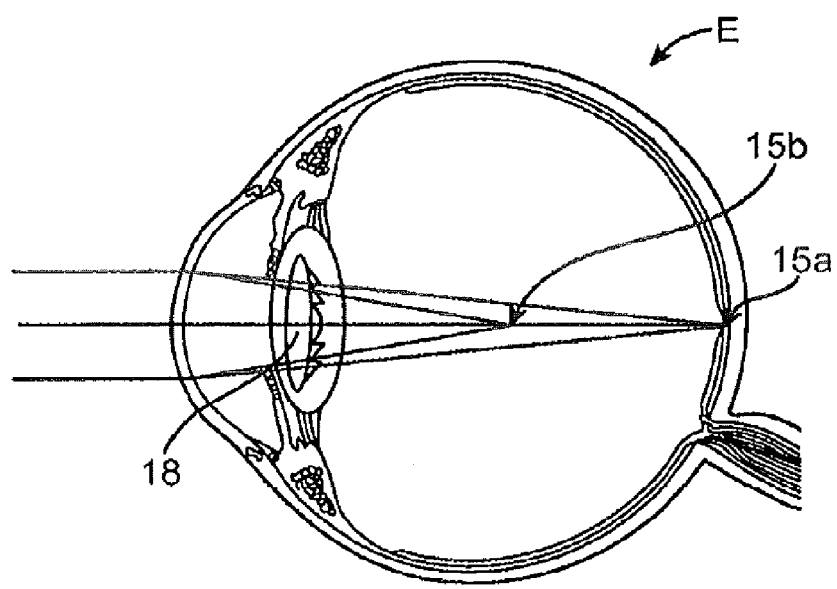
FIG. 1B is a cross-sectional view of an eye having an implanted multifocal intraocular lens.

The corrective optics may also be provided by other types of multifocal ophthalmic lenses such as multifocal intraocular lens (IOL) 18 shown in FIG. 1B. For patients with IOLs, natural lens 14 is removed and IOL 18 is placed within capsular bag 19 in eye E. IOL 18 is centered about the optical axis of the eye E. Like multifocal contact lens 11, IOL 18 often has a refractive power and a diffractive power from a number of concentric diffractive zones. Likewise, IOL 18 focuses incoming light 13 to far field focus 15a and near field focus 15b.

Figure 2A:
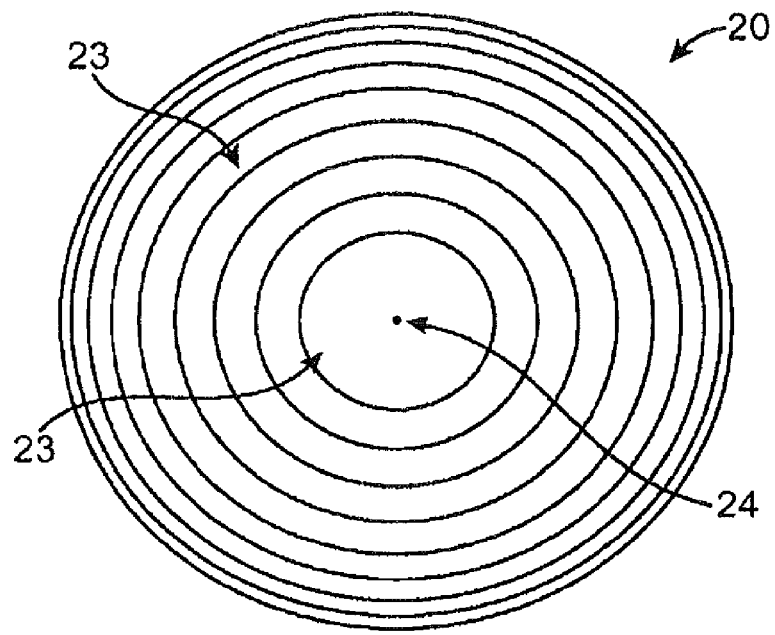
FIG. 2A is a front view of a multifocal ophthalmic lens.
Figure 2B:
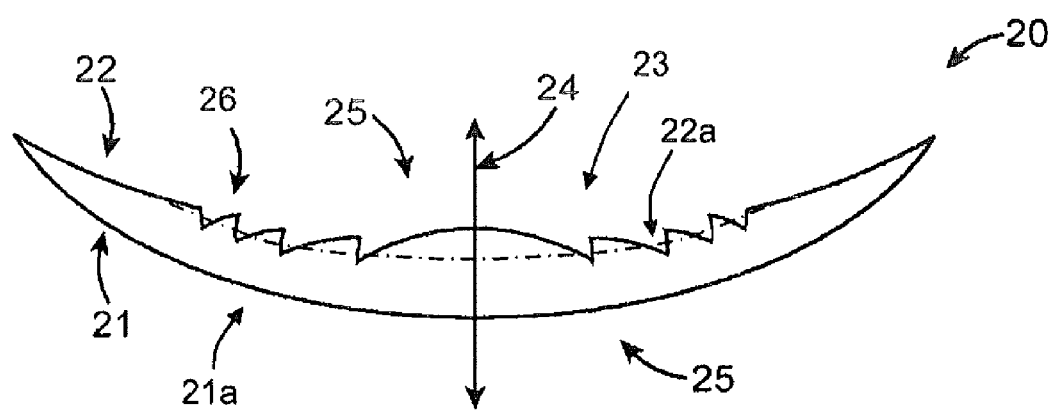
FIG. 2B is a cross-sectional view of the lens of FIG. 2A.

FIGS. 2A and 2B show an exemplary multifoacal lens 20. Multifocal lens 20 has optical properties that may be generally similar to those of multifocal contact lens 11 and IOL 18 described above. Multifocal lens 20 has an anterior lens face 21 and a posterior lens face 22 disposed about optical axis 24. The faces 21, 22 of lens 20 typically define a clear aperture 25. As used herein, the term "clear aperture" means the opening of a lens or optic that restricts the extent of a bundle of light rays from a distant source that can imaged or focused by the lens or optic. The clear aperture is usually circular and is specified by its diameter.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a number of annular optical zones or echelettes 23 spaced about optical axis 24.

Figure 3A:
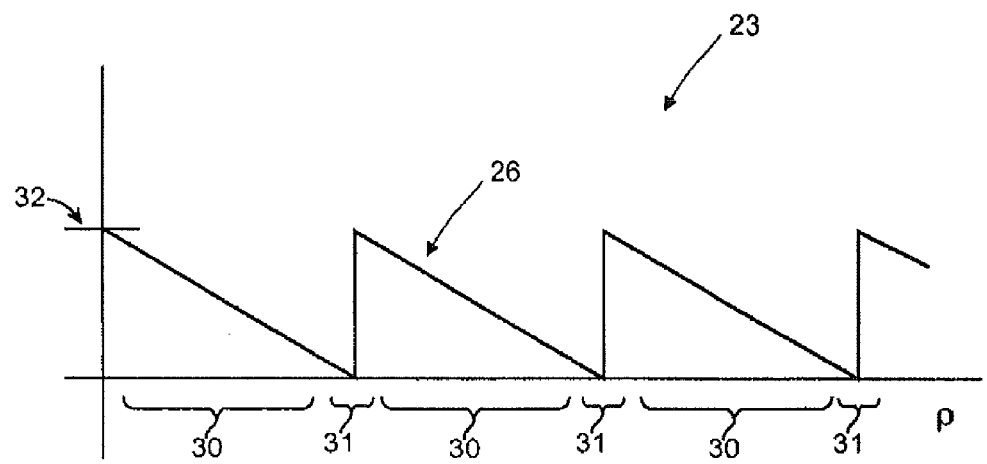
FIG. 3A-3B are graphical representations of a portion of the diffractive profile of a conventional multifocal lens.
Figure 3B:
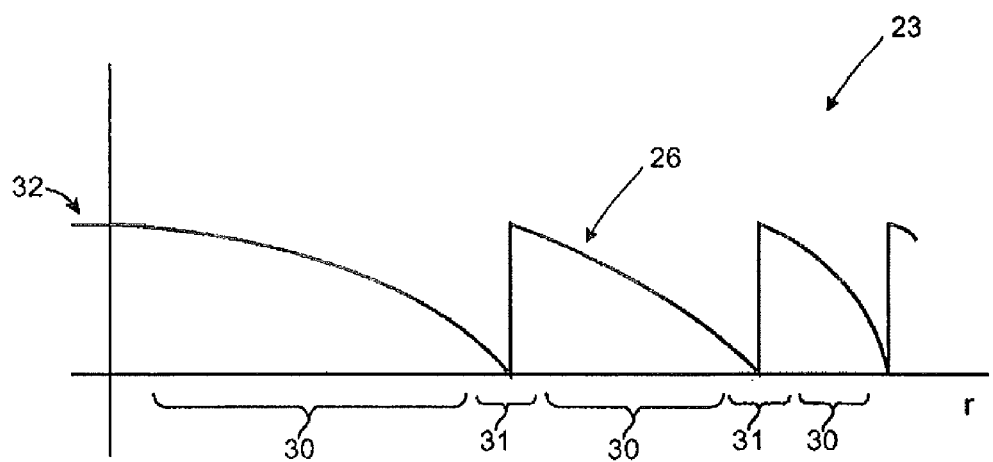

FIGS. 3A and 3B are graphical representation of a portion of the diffractive profile of conventional or reference multifocal lens 20. In FIG. 3A, the displacement (from the optical axis or another reference point on a plane perpendicular to the optical axis) of each point on the echelette surface is plotted against the square of the radial distance ($r^2$ or $\rho$) from the optical axis of the lens. In conventional multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 has a shape or downward slope that may be linear when plotted against $\rho$ as shown in FIG. 3A. When plotted against radius r, optical zone 30 has a shape or downward slope that is parabolic as shown in FIG. 3B. The shape or slope of optical zone 30 determines the add power of lens 20.

As shown in FIGS. 3A and 3B, transition zone 31 between adjacent echelettes is generally sharp and discontinuous. The height of the lens face sharply transitions from sloping steadily downwards to stepping vertically upwards, and the transitions abruptly back to sloping steadily downwards again. In doing so, echelettes 23 also have a characteristic step height 32 defined by the distance between the lowest point and height point of the echelette. Hence, the slope (or first derivative) and/or the curvature (second derivative) of the diffractive surface are discontinuous adjacent the transitions.

The light energy distribution between different diffractive orders is dependent on a wavelength $\lambda$, often in the visible band, the depth of step height 32, and the difference ($\Delta\eta$) between the refractive index of the lens and that of the surrounding medium. For example, step height 32 having a depth of $\lambda$ will distribute the majority of light energy to the $1^{st}$ order, which corresponds to the near field, and essentially be monofocal. At a depth of greater than $\lambda/(2\Delta\eta)$, there will be greater light energy or intensity distributed to the $1^{st}$ order than the $0^{st}$ order, which corresponds to the far field. At a depth of less than $\lambda/(2\Delta\eta)$, light energy is distributed more towards the $0^{th}$ order. Most commonly, a depth of $\lambda/(2\Delta\eta)$ is used for conventional multifocal lenses. At this depth, light energy at the wavelength $\lambda$ can be distributed evenly between the $1^{st}$ and $0^{th}$ orders, often at 40.5% each with the $-1^{st}$ and $2^{nd}$ orders each receiving 4.5% of the light energy.

Figure 4A:
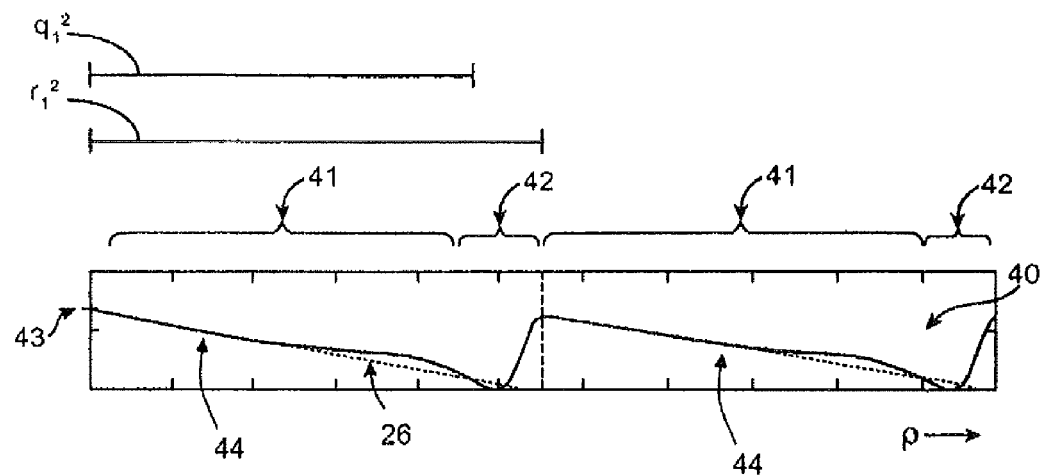
FIG. 4A is a graphical representation of a portion of the diffractive profile of a multifocal lens according to embodiments of the present invention.

FIG. 4A is a graphical representation of a portion of the diffractive profile of a multifocal lens according to an exemplary embodiment of the present invention. The diffractive profile 40 provided by the present invention is generally similar to those shown by FIG. 3A-3B, A multifocal ophthalmic lens with profile 40 is generally similar to the lens shown by FIGS. 2A-2B. Again, the height of each point on the echelette surface is plotted against the square of the radial distance ($r^2$ or $\rho$) from the optical axis of the lens. However, diffractive profile 40 has smooth, continuously curving transition zones 42 between optical zones 41. The smooth, continuous profile reduces the amount of light scatter both by eliminating discontinuities and by reducing the energy in certain predetermined non-viewing orders. Because scatter occurs as a result of light encountering an object (for example, an edge, discontinuity, or in this case, a transition zone) which as the size of about one wavelength of the light, scatter can be reduced by having the radii of curvature of the transition zones larger than the wavelength of incoming light. The total area of the optical zone and smooth transition zone as well as a characteristic step height 43 contribute to the light energy distribution properties of the lens.

The methods described to reduce scatter and optimize light energy distribution are not limited in application to multifocal diffractive lenses. They may also be applicable to monofocal diffractive lenses, for example, those described in U.S. Pat. No. 6,830,332, which is herein incorporated by reference. Monofocal diffractive lenses include a refractive portion and a monofocal diffractive portion. The diffractive portion has a single viewing focus. Implementing a smooth, transition zone having a radius of curvature greater than a design wavelength $\lambda$ would also reduce scatter resulting from the transition zones of the diffractive portion of the monofocal lens. Light distribution may also be balanced between the viewing focus and non-viewing foci using the methods described.

Diffractive profile 40 is shown with a filled line compared to a conventional diffractive profile 44 shown with a parabolic profile shown with a dotted line. See e.g. FIG. 4A. The exemplary diffractive profile is defined by a single, continuous function. In other embodiments, the optical zone and the transition zone may each be defined by distinct functions. The single, continuous function shown is a cosine function enhanced by a power function and a stretch function. See e.g. FIG. 4C. The function, Equation 1 (see also FIG. 4E), is as follows:

$$\Delta(\rho) := \Delta_0 \cdot \left[ \left[ 1 - \left(\frac{\rho}{r_1^2}\right)^{en} \right] \cdot \left[ 1 - \left(\frac{\rho}{r_1^2}\right) \right] \right] + \left[$$

-continued $$\left(\left(\frac{\rho}{r_1^2}\right)\right)^{en}\right]\cdot\left[0.5+0.5\cdot\cos\left[\pi\cdot\frac{\rho}{q_1^2}\cdot\left[1.0+(\rho-q_1^2)\cdot\left[Y\_min+\right.\right.\right.\right.$$
$$\left.\left.\left.\left.(Y\_max-Y\_min)\cdot\left[0.5\cdot\tanh\left[\frac{(\rho-X\_shift)}{m}\right]+0.5\right]\right]\right]\right]\right]$$

$\Delta(\rho)$ is the displacement from a reference plane perpendicular to the optical axis, in other words the height of the profile at a position $\rho$; $\rho$ is the square of radius r from the optical axis; en is an exponential power; $r_1$ is a radius of the first or central echelette; $q_1$ is the size of the optical zone of the first or central echelette ($r_1-q_1$ would therefore be the size of the transition zone); Y_min is a parameter that determines the shape of the optical zone; Y_max is $(2q_1^2-r_1^2)/(r_1^2-q_1^2)/r_1^2$; X_shift is $q_1^2$; m is a parameter indicative of the width of a region blending the optical zone (for the first optical zone, this is when $r<q_1$) and the transition zone (for the first optical zone, this is when $r>q_1$); and $\Delta_0$ is the height of the profile. It will be noted that the term $[1-(\rho/r_1^2)^{en}][1-(\rho/r_1^2)]$ in this equations is an optical zone term that decreases as $\rho$ increases, while the remaining variables to the right of this term form a transition zone term. The addition of optical zone term and the transition term gives the shape of the continuous of the profile.

According to some embodiments, the primary zone and the secondary zone may be defined by distinct functions that smoothly join to one another. The single, continuous function shown in FIG. 4A is a cosine function enhanced by a power function and a stretch function and is shown in FIG. 4C, where $\Delta(\rho)$ is the displacement from a reference plane perpendicular to the optical axis, in other words the height of the profile at a position $\rho$; $\rho$ is the square of a radial distance from the optical axis, en is an exponential power; $r_1$ is a radius of the first or central echelette, $q_1$ affects the size of a primary zone of each echelette, so that $r_1-q_1$ affects the size of a secondary zone of each echelette; Y_min and m are parameters influencing the shape of the echelette; Y_max is $(2q_1^2-r_1^2)/(r_1^2-q_1^2)/r_1^2$; X_shift is $q_1^2$; and $\Delta(\rho)$ is the height of the profile. The primary and secondary zones 41, 42 (optionally referred to as HalfZones) combine to provide a smooth continuous surface, generally free from discontinuities. In some embodiments, the primary zone 41 is characterized by a decreasing zone height with increasing $\rho$, while the secondary zone is characterized by increasing zone height with increasing $\rho$. The exemplary diffractive profile 40 shown in FIG. 4A is characterized by the function shown in FIG. 4C, wherein $\alpha=0.413$, en=0, r1/q1=0.9, m=11 and Y_min= $2*10^{-8}$.

Alternatively, the lens 45 may have a diffractive profile 40' shown in FIG. 4C, which is also characterized by the equation shown in FIG. 4E, wherein $\alpha=0.413$, en=0, r1/q1=0.9, m=1 and Y_min=$2*10^{-8}$. As can be seen, the shape of each echelette 44' can be quite general. As can be seen from the profiles 40, 40', the shape of echelette 44 may be quite general. In the embodiments shown in FIGS. 4A and 4C, shape of echelette 44 is constrained only in that (1) light incident on the lens 45 has a predetermined or desired light distribution between the various diffractive orders of the lens, (2) the shape is a continuous function and (3) the local curvatures are larger than a design wavelength of light. When the light distribution is calculated, the entire profile 40 or surface of the echelette may be taken into account and treated as one optical zone. As an example of the generality possible in defining the profile 40, reference is made to FIG. 4D, where primary zone 41" includes oscillations. In general the continuity between echelettes is met by requiring the echelettes have a continuous form such that the slope and height is the same at the start and the end of each echelette, wherein the form of each echelette is described as by set of connecting continuous curves or functions, the connections being smooth by having the same slope.

The forms of some echelettes are designed in order to have a maximum efficiency in the far and near viewing foci. This may lead to the well-known parabolic shape. As this shape is a discontinuous function, having a step change in height at the end of each echelette, it may pose an issue in that sharp corners are difficult to manufacture, and they can lead to light scatter. This has lead to the introduction of transitions, or transition zones, close to the outer end of the echelette. As a result, these echelettes have a main zone, being the parabolic shape of the actual theoretical design, and a secondary, or transition zone. The secondary or transition zone can be designed to minimize the optically deleterious effects of this transition zone.

According to some embodiments, the echelettes are not divided into zones or sub-zones. Under this description, the form of the total echelette is taken into account when determining the efficiency of the far and near viewing foci, or far, near and adjacent non-viewing foci. Beside the design-requirements concerning the diffractive efficiencies, the form may meet the condition of having the same height and slope at the inner point and the outer point of the echelette. As a result, the form of the echelette will be a continuous function of multiple echelettes. Also, it may deviate totally from the afore mentioned parabolic shape (e.g., profile 23). In some embodiments, the diffractive profile 40 is divided into a primary zone 41 having a negative slope, and a secondary zone 42 having a positive slope. In some embodiments, the profile 40 includes additional zones or sub-zones. The first and second zones 41, 42 (optionally referred to as HalfZones), as well as any additional zones or sub-zones may all be equally important and may each be varied in order to achieve the intended lens performance (e.g., distribution of diffractive efficiencies between diffractive orders of the lens).

The exemplary diffractive profile 40 is characterized by the above function wherein $\alpha=0.592$, en=3, r1/q1=0.95, m=1 and Y_min=$-0.0002$.

In addition to reducing the amount of scatter, diffractive profile 40 results in a different light energy distribution to the diffractive orders, as shown below in Table 1, Compared to a conventional, parabolic diffractive profile which distributes 81.1% of the light energy to the $0^{th}$ and $1^{st}$ orders, diffractive profile 40 distributes less overall energy—here 79.1% of the light energy—to the $0^{th}$ and 1 orders. Also, conventional diffractive profiles distributes 4.5% of the light to the $-1^{st}$ order, the non-viewing order closest to the far focus (i.e., the diffraction efficiency of the $-1$ order is 4.5%). In contrast, diffractive profile 40 distributes less that 4%, often being less than 3%, and preferably less that 2.5% of the incident light energy to the $-1^{st}$ order, with the exemplary embodiment delivering only 2.1% of the light energy (i.e., the diffraction efficiency of the $-1$ order is 2.5%) to the $-1^{st}$ order. This results in less disturbance in far field vision, improving far field quality of vision and reducing dysphotopsia to a lower level.

TABLE 1

| Order | % Light Energy |
|---|---|
| −3 | 2.1% |
| −2 | 2.5% |
| −1 | 2.1% |
| 0 | 39.6% |

TABLE 1-continued

| Order | % Light Energy |
|---|---|
| 1 | 39.5% |
| 2 | 6.5% |
| 3 | 1.1% |

Figure 4B:
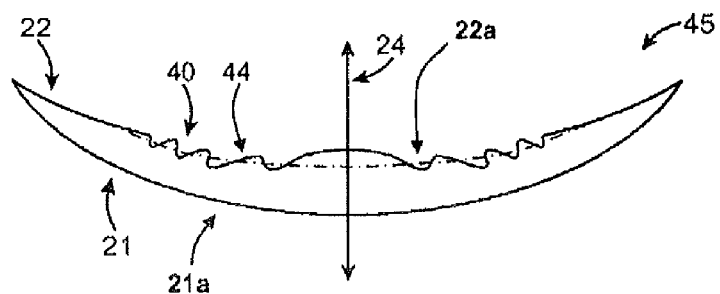
FIG. 4B is a cross-sectional view of a multifocal ophthalmic lens having the diffractive profile shown by FIG. 4A.
Figure 4C:
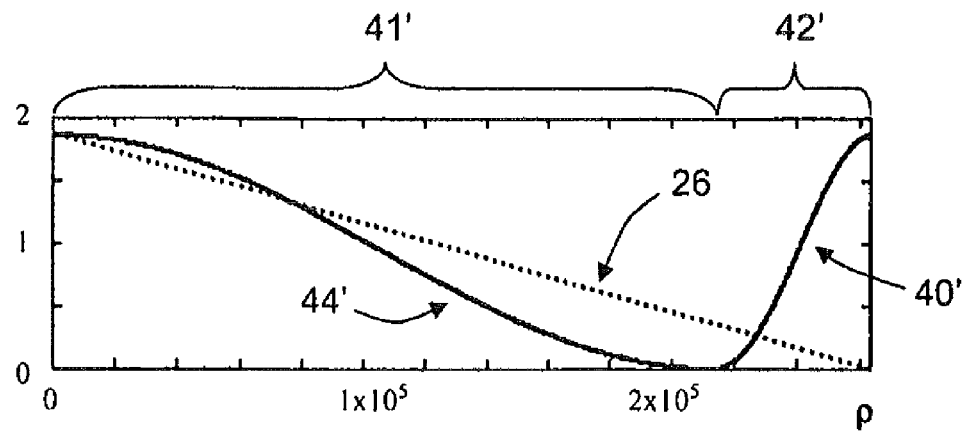
FIG. 4C is a cross-sectional view of a multifocal ophthalmic lens having the diffractive profile according to another embodiment of the present invention.
Figure 4D:
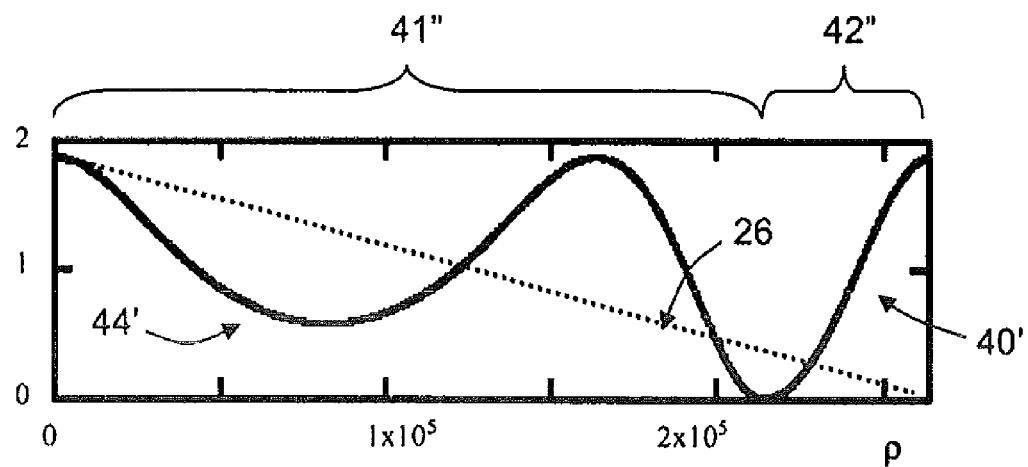
FIG. 4D is a cross-sectional view of a multifocal ophthalmic lens having the diffractive profile according to another embodiment of the present invention.

FIG. 4B schematically shows a multifocal ophthalmic lens 45 having diffractive profile 40 of FIG. 4A. Like the conventional ophthalmic lens 20 of FIG. 2B, multifocal ophthalmic lens 45 has an anterior lens face 21 and a posterior lens face 22, each having a refractive profile based on its curvature and material from which it is made. The lens faces are disposed about optical axis 24 and define a clear aperture 25. Diffractive profile 40 is imposed on posterior lens face 22. Diffractive profile 40 is defined by a number of echelettes 46 concentrically spaced about optical axis 24.

In some aspects, embodiments of the present invention encompass ophthalmic lenses that involve a displacement function based on the sum of continuous cosine and sine functions, as well as methods of their use and manufacture. For example, an ophthalmic lens may include an anterior face having an anterior refractive profile, and a posterior face having a posterior refractive profile. The anterior and posterior faces can be disposed about an optical axis. The lens may include a diffractive profile imposed on one of the refractive profiles. The diffractive profile may include a plurality of echelettes, and may be characterized by a displacement function over the plurality of echelettes. The displacement function can be based the sum of a continuous cosine function and a continuous sine function over the plurality of echelettes. FIG. 4F shows an exemplary equation for a displacement function having such attributes. As depicted in Equation 2 below, the displacement function $\Delta(\rho)$ of FIG. 4F is equal to a continuous cosine function over a plurality of echelettes, for example:

$$\Delta\_1(\rho) \cdot \left[1 - \left[Y\min + (Y\max - Y\min) \cdot \left(C_3 + C_4 \cdot \tanh\left(\frac{\sqrt{\rho} \, X\_shift}{Width}\right) + w\right)\right]\right]$$

(cosine function)

added to a continuous sine function over a plurality of echelettes, for example:

$$\Delta\_2(\rho) \cdot \left[Y\min + (Y\max - Y\min) \cdot \left(C_3 + C_4 \cdot \tanh\left(\frac{\sqrt{\rho} \, X\_shift}{Width}\right) + w\right)\right]$$

(sine function).

As shown here, the cosine function can be a product of two multiplicands. The first multiplicand of the cosine function, $\Delta\_1(\rho)$, can be expressed as follows:

$$\Delta\_1(\rho) := v\Delta_{01} \cdot \left[\left[C_1 + C_2 \cdot \cos\left[\pi \cdot \left[\frac{(\rho)}{q1^2}\right]\right]\right]\right]$$

where:
v=variable [e.g. 0.775],
$\Delta_{01} = (\lambda/(n_{iol} - n_{med})) * \alpha$,
$\alpha = 1.086 * u$,
u=variable,
$\lambda$ represents a design wavelength,
$n_{iol}$ is the refractive index of the ophthalmic lens,
$n_{med}$ is the refractive index of the eye,
$C_1$=variable,
$C_2$=variable,
$\rho$ is square of the radius from the optical axis, and
$q_1$ is the size of an optical zone of a first or central echelette.

The second multiplicand of the cosine function can be expressed as follows:

[1−[Ymin+(Ymax−Ymin)($C_3$+$C_4$*tan h(
$\sqrt{\rho}$−X_shift)/Width)+w)]]

where:
Ymin is a parameter that affects the shape of the optical zone,
Ymax=$(2q_1^2 - r_1^2)/(r_1^2 - q_1^2)/r_1^2$,
$q_1$ is the size of an optical zone of a first or central echelette,
$r_1$ is a radius of a first or central echelette,
$(r_1 - q_1)$ is the size (e.g. radial width) of a transition zone,
X_shift=$q_1^2$,
$C_3$=variable,
$C_4$=variable,
Width is a parameter indicative of a width of a region blending the optical zone (e.g. for a first optical zone, when r<$q_1$) and the transition zone (e.g. for a first optical zone, when r>$q_1$), and
w is a smoothing parameter.

Similarly, the sine function can be a product of two multiplicands. The first multiplicand of the sine function, $\Delta\_2(\rho)$, can be expressed as follows:

$$\Delta\_2(\rho) := v\Delta_{01} \cdot \left[\left[C_1 + C_2 \cdot \sin\left[\pi \cdot \left[\frac{\rho - \frac{(r_1^2 + q1^2)}{2}}{(r_1^2 - q1^2)}\right]\right]\right]\right]$$

where:
v=variable [e.g. 0.775],
$\Delta_{01} = (\lambda/(n_{iol} - n_{med})) * \alpha$,
$\alpha = 1.086 * u$,
u=variable,
$\lambda$ represents a design wavelength,
$n_{iol}$ is the refractive index of the ophthalmic lens,
$n_{med}$ is the refractive index of the eye,
$C_1$=variable,
$C_2$=variable,
$\rho$ is square of the radius from the optical axis, and
$q_1$ is the size of an optical zone of a first or central echelette.

The second multiplicand of the sine function can be expressed as follows:

[Ymin+(Ymax−Ymin)($C_3$+$C_4$*tan h(
$\sqrt{\rho}$−X_shift)/Width)+w)]

where:
Ymin is a parameter that affects the shape of the optical zone,
Ymax=$(2q_1^2 - r_1^2)/(r_1^2 - q_1^2)/r_1^2$,
$q_1$ is the size of an optical zone of a first or central echelette,
$r_1$ is a radius of a first or central echelette,
$(r_1 - q_1)$ is the size (e.g. radial width) of a transition zone,
X_shift=$q_1^2$,
$C_3$=variable,
$C_4$=variable,
Width is a parameter indicative of a width of a region blending the optical zone (e.g. for a first optical zone, when r<$q_1$) and the transition zone (e.g. for a first optical zone, when r>$q_1$), and
w is a smoothing parameter.

According to some embodiments, the $C_1$ and/or $C_2$ variables in the first multiplicands can operate to provide enhanced displacement profiles for distance and near vision. What is more, the $C_3$ and/or $C_4$ variables in the second multiplicands can operate to enhance the displacement profile and corresponding efficiencies at each diffraction order.

Figure 4G:
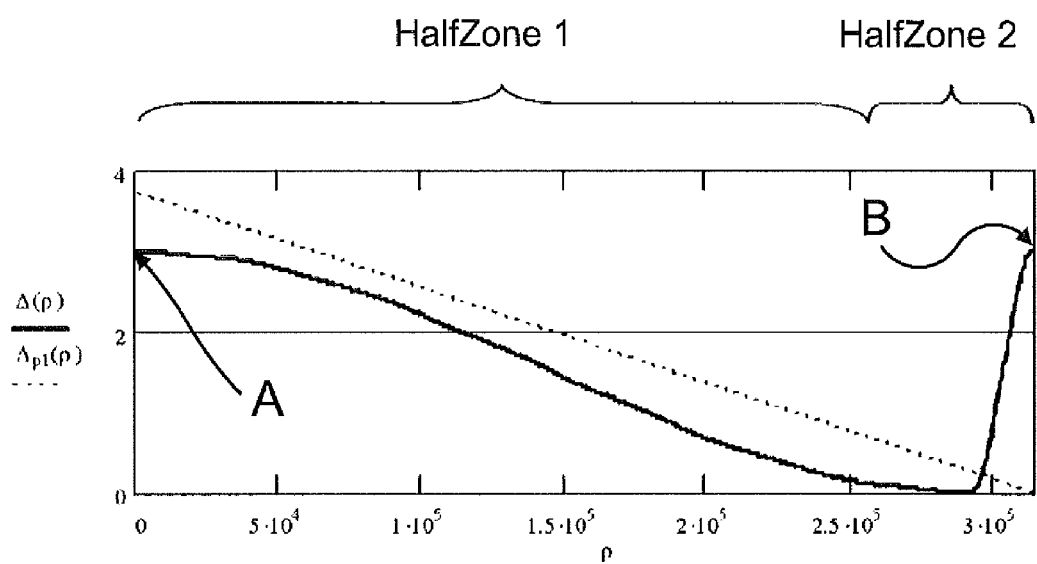
FIG. 4G depicts a graph of a diffractive profile or displacement function for a lens according to embodiments of the present invention.

FIG. 4G shows a graph of a diffractive profile or displacement function, $\Delta(\rho)$ as a function of $\rho$, (solid line), according to the equation of FIG. 4F, computed with the parameters shown in Table A. The term "HalfZone 1" can refer to a profile corresponding to the continuous cosine function $\Delta\_1(\rho)$ and the term "HalfZone 2" can refer to a profile corresponding to the continuous sine function $\Delta\_2(\rho)$. According to some embodiments, the shape characterized in FIG. 4G can provide an efficiency for a real image that is 90% or higher, and can also provide improved manufacturability features.

For the cosine and sine first multiplicands, $\Delta\_1(\rho)$ and $\Delta\_2(\rho)$ respectively, the following parameters were used:

TABLE A (First Multiplicands: for FIG. 4G)

| Parameters | Cosine 1$^{st}$ Multiplicand: $\Delta\_1(\rho)$ | Sine 1$^{st}$ Multiplicand: $\Delta\_2(\rho)$ |
|---|---|---|
| $\mu$ | 0.956 | 0.956 |
| $\alpha$ | 1.086*$\mu$ | 1.086*$\mu$ |
| $\alpha$ | 1.038216 | 1.038216 |
| $\lambda$ | 0.55 microns | 0.55 microns |
| $n_{iol}$ | 1.47 | 1.47 |
| $n_{med}$ | 1.336 | 1.336 |
| $\Delta_{01}$ | 3.8739402985074626866 | 3.8739402985074626866 |
| $\rho$ | square of radius from optical axis | square of radius from optical axis |
| $q_1$ | optical zone size, 1st or central echelette | optical zone size, 1st or central echelette |
| v | between 0.2 and 10 (e.g. about 0.75) | between 0.2 and 10 (e.g. about 0.75) |
| C1 | between 0 and 1 | between 0 and 1 |
| C2 | between 0 and 1 | between 0 and 1 |

For the cosine and sine second multiplicands, the following parameters were used:

TABLE B (Second Multiplicands: for FIG. 4G)

| Parameters | Cosine F$^{cn}$ Second Multiplicand | Sine F$^{cn}$ Second Multiplicand |
|---|---|---|
| Ymin | −0.0000209 | −0.0000209 |
| Ymax | 1.0 | 1.0 |
| $\rho$ | square of radius from optical axis | square of radius from optical axis |
| X_shift | $q_1^2$ | $q_1^2$ |
| Width | 0.00001 | 0.00001 |
| w | 0.01 | 0.01 |
| C3 | between 0 and 1 | between 0 and 1 |
| C4 | between 0 and 1 | between 0 and 1 |

By selecting appropriate values for certain parameters or variables of the displacement function is possible to individually weight the continuous cosine and sine functions relative to one another.

Values selected for the smoothing parameters w of the second multiplicands enable the displacement profile to provide a smooth connection between adjacent zones. For example, by selecting appropriate values for the w parameter, it is possible to provide a continuity between zones, such that the value of $[\Delta(\rho)/\Delta_{p1}(\rho)]$ is equivalent at points A and B. In some instances, the value for w is 0.01. In some instances, the value for w is 0.55.

Also shown in FIG. 4G is a conventional diffractive profile, $\Delta_{p1}(\rho)$ as a function of $\rho$, (dashed line), calculated as follows:

$$\Delta_{p1}(\rho) := \frac{\lambda}{n_{iol} - n_{med}} \cdot \left[1 - \left(\frac{\rho}{r_1^2}\right)\right]$$

where:

$\rho$ represents a design wavelength, $n_{iol}$ is the refractive index of the ophthalmic lens, $n_{med}$ is the refractive index of the eye, $\rho$ is square of the radius from the optical axis, and $r_1$ is a radius of a first or central echelette.

As depicted in FIG. 4G, the reference, or dashed line, is parabolic.

Figure 4H:
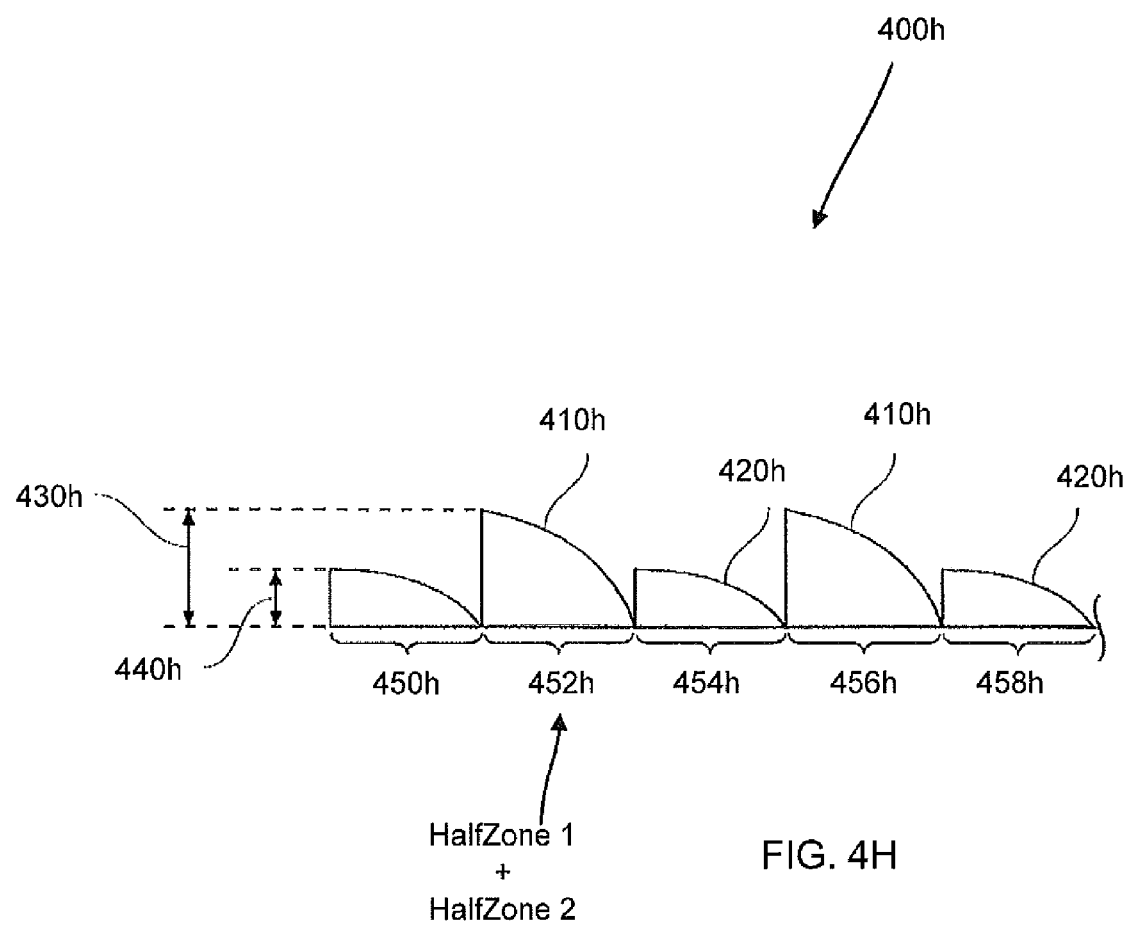
FIG. 4H shows a portion of a diffractive profile of diffractive structure for a lens according to embodiments of the present invention.

FIG. 4H shows a portion of a diffractive profile of diffractive structure 400h, where a first plurality of echelettes 410h provides substantially monofocal diffractive profiles for near vision correction and a second plurality of echelettes 420h provides substantially bifocal, quadfocal, or otherwise multifocal diffractive profiles for far vision correction and near vision correction. The first plurality of echelettes 410h can have a step height 430h, and the second plurality of echelettes 420h can have a step height 440h. The diffractive structure 400h also provides full period zones 450h, 452h, 454h, 456h, and 458h corresponding to the echelettes. As noted above, the term "HalfZone 1" can refer to a profile corresponding to the continuous cosine function $\Delta\_1(\rho)$ and the term "HalfZone 2" can refer to a profile corresponding to the continuous sine function $\Delta\_2(\rho)$. Hence, a full period zone (e.g. 452h) can correspond to a HalfZone 1 combined with a HalfZone 2. Embodiments of the present invention encompass diffractive structures where each echelette corresponding to the individual zones 450h, 452h, 454h, 456h, and 458h may have a unique step height. For example, the echelettes of zones 450h, 452h, 454h, 456h, and 458h may have heights H1, H2, H3, H4, and H5, respectively, where each of the heights has a value that is different from the other height values.

Embodiments of the present invention encompass multifocal designs which may present, for example, scattering levels no more than 10%. In some instances, it is possible to use the equation of FIG. 4F to obtain such results, for example by selecting appropriate values for u, v, $C_1$, $C_2$, $C_3$, and/or $C_4$.

According to one embodiment, as shown in Table C, the distance vision or zero order diffraction value is about 80.5%, and the near vision or first order diffraction value is about 10%. The scattering is less than or equal to about 10%.

TABLE C (Test Case 1)

| Order | % Light Energy |
|---|---|
| −3 | 0.08% |
| −2 | 0.38% |
| −1 | 8.53% |
| 0 | 80.56% |
| 1 | 9.87% |
| 2 | 0.03% |
| 3 | 0.1% |

According to another embodiment, as shown in Table D, the distance vision or zero order diffraction value is about 2.2%, and the near vision or first order diffraction value is about 88.4%. The scattering is less than about 10%.

TABLE D (Test Case 2)

| Order | % Light Energy |
|---|---|
| −3 | 0.66% |
| −2 | 1.27% |
| −1 | 2.68% |
| 0 | 2.19% |
| 1 | 88.39% |
| 2 | 0.35% |
| 3 | 0.74% |

In another design, test cases 1 and 2 may be combined together alternatively with the same add power—>distance 41.35%, near 49.2%, and the scattering=9.45%, that is, less than 10%.

Embodiments of the present invention encompass bifocal optic designs that provide at least about 90% efficiency to two viewing orders. Such efficiencies with a bifocal diffractive represent a significant improvement over previously described designs.

Figure 5A:
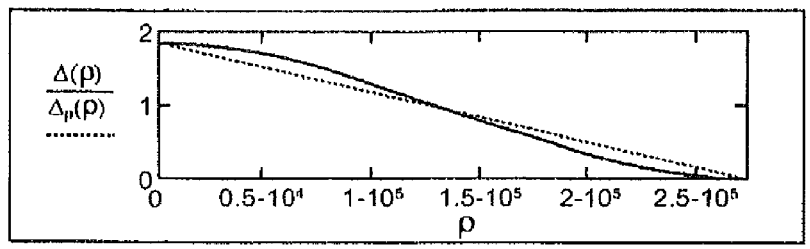
FIGS. 5A through 5I show graphs of diffractive profiles of multifocal lenses according to embodiments of the present invention.
Figure 5B:
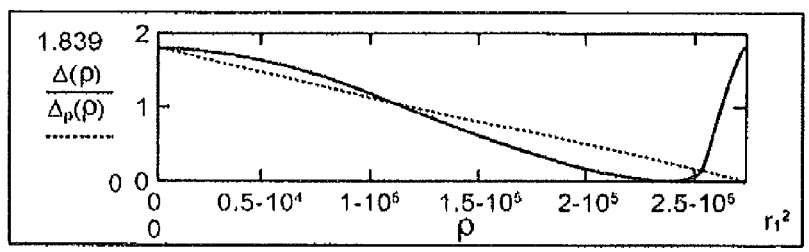
Figure 5C:
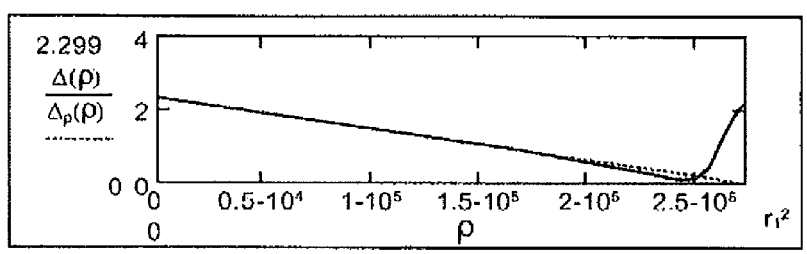
Figure 5D:
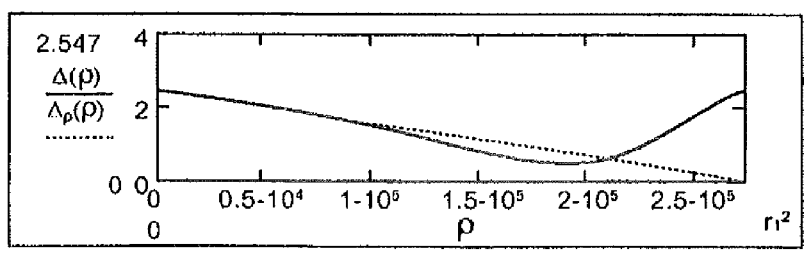
Figure 5E:
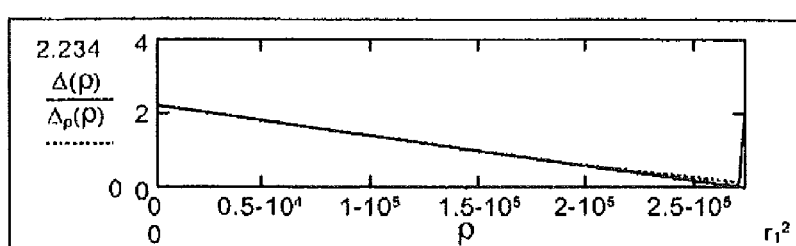
Figure 5F:
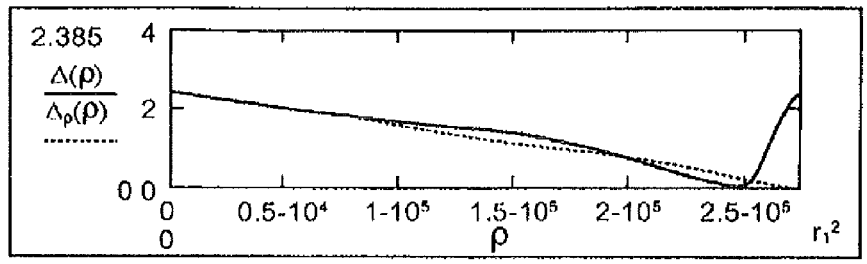
Figure 5G:
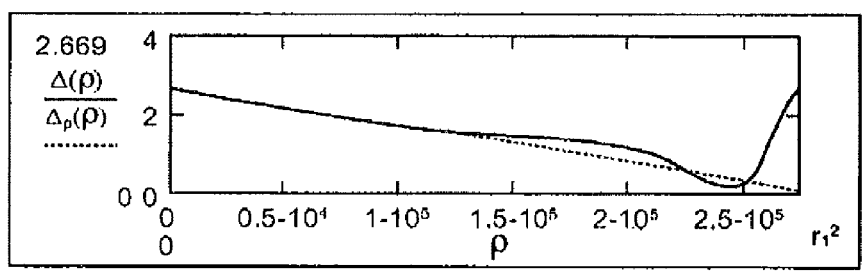
Figure 5H:
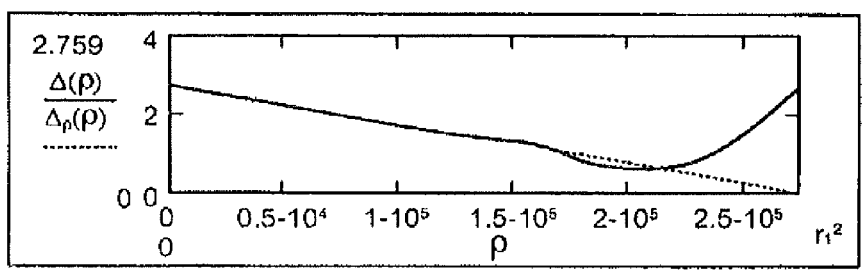
Figure 5I:
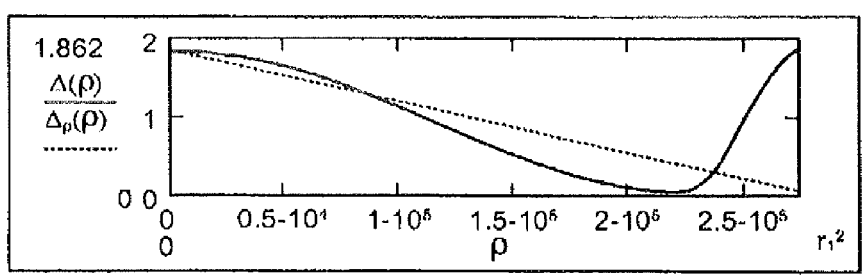

FIGS. 5A through 5I shows graphs of diffractive profiles according to Equation 2 (FIG. 4F) computed with the parameters shown below in Table 2. Table 2 shows the light distribution per diffractive order for the various diffractive profiles shown by FIGS. 5A-5I. FIG. 5A shows profile code 0-2 from the table, FIG. 5B shows profile code 0-3, FIG. 5C shows profile code 4-1; FIG. 5D shows profile code 4-2; FIG. 5E shows profile code 4-3; FIG. 5F shows profile code 4-4; FIG. 5G shows profile code 4-5; FIG. 5H shows profile code 4-6; FIG. 5I shows profile code 4-7. FIGS. 5A through 5I also include the conventional diffractive profile (code 0-1 in Table 2) shown as a dotted line.

Profile 4-5 corresponding to diffractive profile 40 of FIG. 4 has a diffraction efficiency of the −1 order of 2.1%. Profile 0-1 corresponding to a conventional parabolic profile has a diffraction efficiency of the −1 order of 4.5%. Although not shown, other parameters used for function 1 may result in profiles other than profile 4-5 having a diffraction efficiency of the −1 order of less than 4.5%, preferably less than 4%, and more preferably less than 2.5%.

Figure 6A:
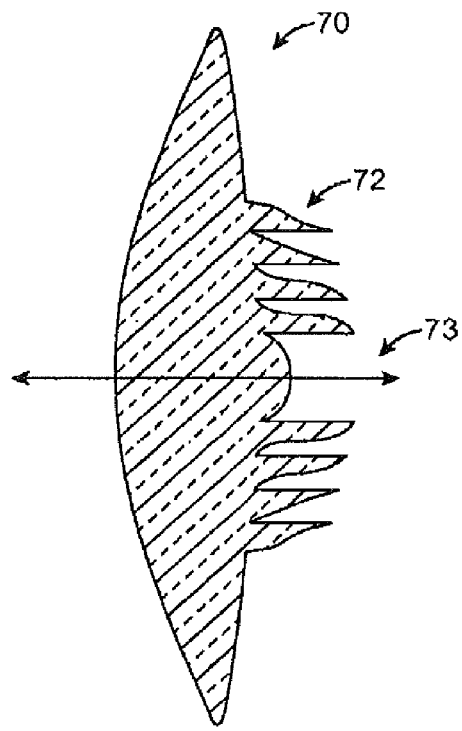
FIG. 6A is a cross-sectional view of a multifocal lens according to embodiments of the present invention having constant step height of the transition zones and varying shapes of the optical zones with radius.
Figure 6B:
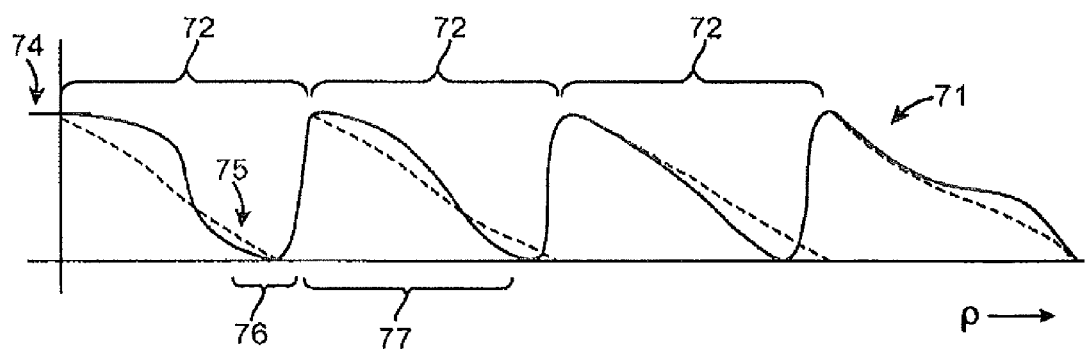
FIG. 6B is a graphical representation of the diffractive profile of the lens of FIG. 7A.
Figure 7A:
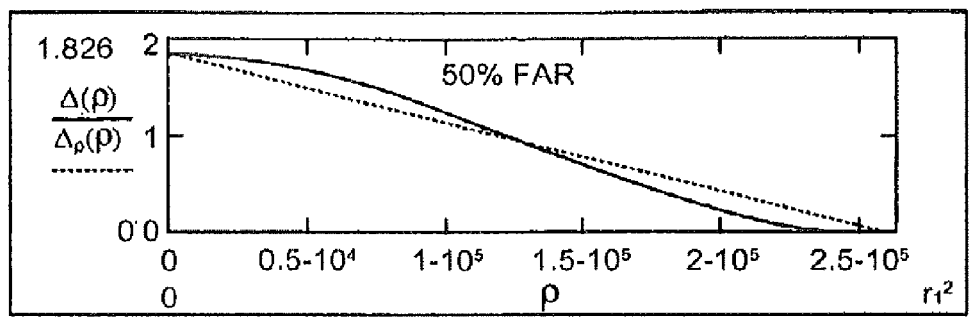
FIG. 7A-7D show graphs of the diffractive profiles of individual echelettes according to embodiments of the present invention.
Figure 7B:
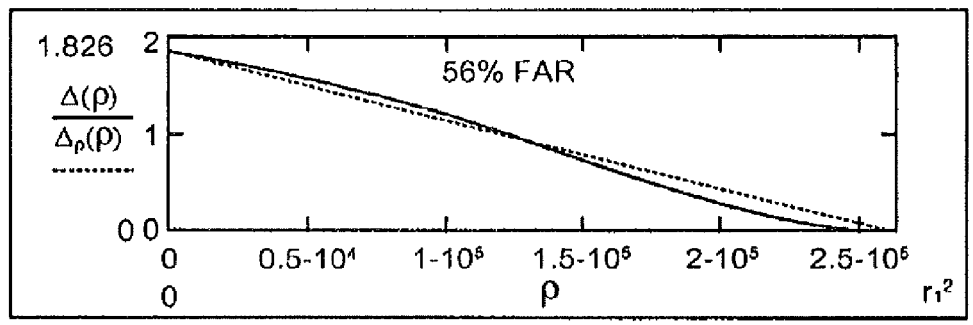
Figure 7C:
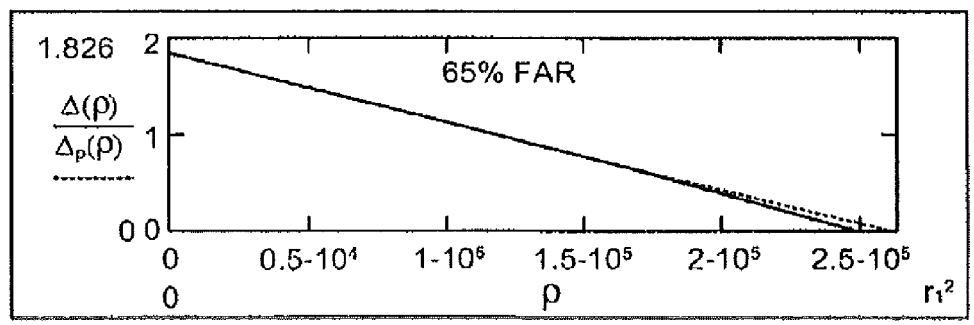
Figure 7D:
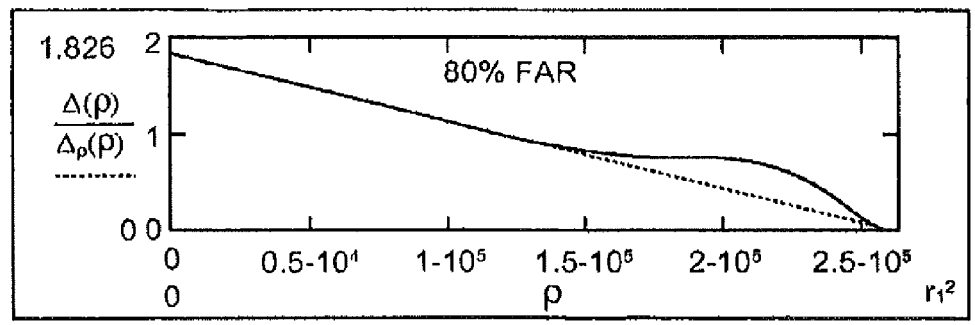

FIG. 6A shows a cross-sectional view of an alternative multifocal ophthalmic lens 70. Like previously described multifocal, ophthalmic lenses, lens 70 comprises a number of echelettes 72 spaced about optical axis 73. Echelettes 72 each have an optical zone and a transition zone, Echelettes 72 of lens 70 each share a common step height 74. However, as seen in FIG. 6B, each echelette 71 has a different shape, which changes the diffractive efficiency of each echelette. Hence, lens 70 may provide pupil-dependent variable imaging energy distribution similar to that of variable step height or apodization (including those described in U.S. Pat. No. 5,699,142 in the name of Lee et al.), but without progressive variations in step height.

FIG. 6B is a graphical representation of the diffractive profile 71 of lens 70, plotting the height of lens 70 at a particular point of echelette 72 versus ρ, the square of the radius or distance displaced from the optical axis, and shown with conventional diffractive profile 75, shown by the dotted line. FIG. 7A-7D show graphs of the diffractive profiles of individual echelettes and the diffractive efficiency in the far focus order. Optical zone 77 and transition zone 76 of each echelette 71 can be defined by Equation 1 but each using a different set of parameters. FIGS. 7A, 7B, 7C and 7D show the diffractive profiles of an echelettes having a diffractive efficiency of approximately 50%, 56%, 65% and 80%, respectively, in the far focus. Table 3A below shows a number of echelettes 71 each having a different diffractive efficiency depending on the parameters used for Function 1. Table 3B shows the parameters used and the resulting diffraction efficiency for the far focus as well as the percentage of light energy lost to higher order, non-viewing foci. The diffraction efficiencies were calculated using MATHCAD, available from Parametric Technology Corporation of Needham, Mass.

TABLE 3A

| | Focus Order | | | | | | |
|---|---|---|---|---|---|---|---|
| Echelette | −3 | −2 | −1 | 0 | 1 | 2 | 3 |
| 1 | 1.0% | 2.3% | 7.9% | 40.2% | 40.2% | 2.0% | 1.1% |
| 2 | 1.0% | 2.3% | 7.8% | 41.6% | 39.0% | 2.1% | 1.1% |

TABLE 2

| | Profile Code | | | | | | | | | |
|---|---|---|---|---|---|---|---|---|---|---|
| | 0-1 | 0-2 | 0-3 | 4-1 | 4-2 | 4-3 | 4-4 | 4-5 | 4-6 | 4-7 |
| Order | Parabolic | Parabolic with Cosine ending | Parabolic with Cosine ending | Parabolic with Cosine ending | Parabolic with Cosine ending | Parabolic with Cosine ending | Parabolic with Cosine ending | Parabolic with Cosine ending | Parabolic with Cosine ending | Parabolic with Cosine ending |
| −3 | 0.8% | 1.0% | 1.8% | 1.9% | 2.2% | 1.0% | 2.0% | 2.1% | 3.0% | 2.0% |
| −2 | 1.6% | 2.3% | 3.6% | 3.1% | 6.2% | 1.9% | 3.3% | 2.5% | 6.4% | 4.7% |
| −1 | 4.5% | 7.9% | 10.9% | 5.8% | 15.6% | 4.7% | 4.5% | 2.1% | 10.3% | 14.2% |
| 0 | 40.5% | 40.3% | 39.6% | 40.3% | 37.3% | 40.6% | 39.5% | 39.6% | 38.8% | 38.6% |
| 1 | 40.5% | 40.2% | 39.6% | 40.3% | 37.4% | 40.5% | 39.5% | 39.5% | 38.9% | 38.5% |
| 2 | 4.5% | 2.0% | 0.7% | 3.2% | 0.1% | 4.3% | 5.2% | 6.5% | 0.3% | 0.0% |
| 3 | 1.6% | 1.0% | 0.4% | 0.5% | 0.2% | 1.4% | 0.5% | 1.1% | 0.2% | 0.1% |
| | Parameters | | | | | | | | | |
| α | 0.5 | 0.405 | 0.408 | 0.5115 | 0.565 | 0.4955 | 0.529 | 0.592 | 0.621 | 0.413 |
| en | n/a | n/a | 0 | 4 | 2 | 10 | 2 | 3 | 5 | 0 |
| $r_1/q_1$ | n/a | n/a | 0.95 | 0.95 | 0.8 | 0.99 | 0.95 | 0.95 | 0.81 | 0.9 |
| m | n/a | n/a | 1 | 1 | 1 | 1 | 1 | 1 | 1 | 1 |
| Y_min | n/a | n/a | 0 | 2.5E−6 | 0 | 0 | 5E−06 | −2E−05 | 4E−05 | 2E−08 |

TABLE 3A-continued

| | Focus Order | | | | | | |
|---|---|---|---|---|---|---|---|
| Echelette | −3 | −2 | −1 | 0 | 1 | 2 | 3 |
| 3 | 1.0% | 2.2% | 7.8% | 43.0% | 37.8% | 2.2% | 1.1% |
| 4 | 1.0% | 2.1% | 7.4% | 44.0% | 36.9% | 2.3% | 1.1% |
| 5 | 0.9% | 2.1% | 7.1% | 45.4% | 35.7% | 2.4% | 1.1% |
| 6 | 0.9% | 2.0% | 6.9% | 46.6% | 34.6% | 2.6% | 1.2% |
| 7 | 0.9% | 1.9% | 6.5% | 48.0% | 33.4% | 2.8% | 1.2% |
| 8 | 0.9% | 1.9% | 6.1% | 49.4% | 32.2% | 3.1% | 1.2% |
| 9 | 0.9% | 1.9% | 5.6% | 50.8% | 31.0% | 3.4% | 1.2% |
| 10 | 0.9% | 1.9% | 5.2% | 52.0% | 29.9% | 3.6% | 1.3% |
| 11 | 0.9% | 1.8% | 4.8% | 53.4% | 28.7% | 3.8% | 1.3% |
| 12 | 0.9% | 1.6% | 4.1% | 56.5% | 25.9% | 4.2% | 1.5% |
| 13 | 0.8% | 1.4% | 3.4% | 60.2% | 22.6% | 4.5% | 1.7% |
| 14 | 0.8% | 1.1% | 2.9% | 63.4% | 19.7% | 4.6% | 2.0% |
| 15 | 0.7% | 0.8% | 2.7% | 66.8% | 16.6% | 4.3% | 2.2% |
| 32 | 0.7% | 0.8% | 2.7% | 66.8% | 16.6% | 4.3% | 2.2% |

TABLE 3B

| Echelette | α | en | $r_1/q_1$ | m | Y_min | % Far | Loss |
|---|---|---|---|---|---|---|---|
| 1 | 0.4075 | 0 | 0.9999 | 10 | 0.0000001 | 50% | 20% |
| 2 | 0.4075 | 0.09 | 0.9999 | 10 | 0.0000001 | 51.6% | 19% |
| 3 | 0.4075 | 0.2 | 0.9999 | 10 | 0.0000001 | 53.2% | 19% |
| 4 | 0.4075 | 0.3 | 0.9999 | 10 | 0.0000001 | 54.4% | 19% |
| 5 | 0.4075 | 0.46 | 0.9999 | 10 | 0.0000001 | 56.0% | 19% |
| 6 | 0.4075 | 0.63 | 0.9999 | 10 | 0.0000001 | 57.4% | 19% |
| 7 | 0.4075 | 0.9 | 0.9999 | 10 | 0.0000001 | 58.9% | 19% |
| 8 | 0.4075 | 1.3 | 0.9999 | 10 | 0.0000001 | 60.5% | 18% |
| 9 | 0.4075 | 2 | 0.9999 | 10 | 0.0000001 | 62.1% | 18% |
| 10 | 0.4075 | 3 | 0.9999 | 10 | 0.0000001 | 63.5% | 18% |
| 11 | 0.4075 | 5 | 0.9999 | 10 | 0.0000001 | 65.0% | 18% |
| 12 | 0.4075 | 5 | 0.9999 | 10 | 0.000003 | 68.5% | 18% |
| 13 | 0.4075 | 5 | 0.9999 | 10 | 0.000006 | 72.7% | 17% |
| 14 | 0.4075 | 5 | 0.9999 | 10 | 0.0000036 | 76.3% | 17% |
| 15 | 0.4075 | 5 | 0.9999 | 10 | 0.0000118 | 80% | 17% |
| 32 | 0.4075 | 5 | 0.9999 | 10 | 0.0000118 | 80% | 17% |

As seen from Tables 3A and 3B, by gradually varying the shape of each echelette as a function of distance or radius from the optical axis, the diffraction efficiency for the $0^{th}$ order or far focus is gradually increased from 50% to 80%.

The results from Tables 3A and 3B are exemplary of the benefits provided by a multifocal lens, such as the multifocal lens 70, in which at least one echelette surrounding a central echelette has an echelette form that is different from the echelette form of the remaining echelettes surrounding the central echelette. As used herein, the term "echelette form" may mean the shape of the profile of the echelette when plotted verses radius squared ($r^2$ or ρ) from the optical axis of an optic containing the echelette. Two echelettes are considered to have the same echelette form if profiles of each verses radius squared is the same when normalized to the echelette height. For example, each of the echelettes of an apodized diffraction grating may be considered to generally have the same echelette forms. By contrast, the echelettes in FIGS. 5A-5I or Tables 3B are examples of echelettes having echelette forms that are not equal to one another, since the form of any one of these echelettes could not be made equal to the others by a simple linear scaling constant.

In some embodiments, a diffractive lens is made of a gradient index material having a refractive index that changes with increasing radius from the optical axis (e.g., the lens may have a refractive index that decrease with increasing radius from the optical axis). In any such embodiments, the refractive index change effectively changes the optical path length of the lens with increasing radius from the optical axis. Such a lens material may be used with any of the lenses or profiles discussed above herein to provide an additional design parameter for controlling the optical performance (e.g., the diffraction efficiencies of various diffractive orders) of a diffractive lens. Examples of the use of gradient materials in ophthalmic lenses is discussed in the article titled "Radial gradient index intraocular lens: a theoretical model" (Damian Siedlecki, et al., Journal of Modern Optics, Vol. 55, Nos. 4-5, 20 Feb.-10 Mar. 2008, 639-647), which is herein incorporated by reference in its entirety. For example, such a material could be used with any of the lenses discussed and shown herein. In some embodiments, the gradient index material is used with an otherwise conventional diffractive lens. In some embodiments, the step height or echelette height is varied in combination with the gradient index to adjust the energy going into specific diffraction orders of the lens or to change the diffraction efficiency of the echelettes or the overall diffraction efficiency of the lens with increasing radius from the optical axis of the lens. In addition, the lens material and the diffractive profile may be configured so that the diffractive lens has a negative spherical aberration or some other aberration, for example, to correct for a positive spherical aberration or some other aberration of a surface of the lens and/or of a cornea into which the lens is placed or inserted.

Embodiments of the present invention may incorporate standard techniques for the manufacture of intraocular lenses, aspects of which are described in U.S. Pat. Nos. 4,856,234, 5,322,649, and 5,888,122, as well as U.S. Patent Publication No. 2002/0082690. The content of each of these patent publications is incorporated herein by reference. Relatedly, in some instances manufacturing processes may include aspects of molding, polishing, measuring of the power, quality control, and the like.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

The embodiments described above, including accompanying drawings, figures, functions and tables, are for illustrative purposes to explain aspects of the present invention. Those skilled in the art will recognize that changes and modifications can be made without departing from the scope of the invention, which is solely limited by the claims as follows.

What is claimed is:

1. An ophthalmic lens, comprising:
an anterior face with an anterior refractive profile and a posterior face with a posterior refractive profile, the faces disposed about an optical axis;
a diffractive profile imposed on one of the refractive profiles, the diffractive profile comprising a plurality of echelettes, the diffractive profile characterized by a displacement function over the plurality of echelettes, the displacement function comprising the sum of a continuous cosine function and a continuous sine function over the plurality of echelettes,
wherein the diffractive profile provides a light scatter characteristic that scatters less than 5% of light.

2. The ophthalmic lens according to claim 1, wherein the continuous sine function is affected by a hyperbolic tangent function.

3. The ophthalmic lens according to claim 1, wherein the continuous cosine function is affected by a hyperbolic tangent function.

4. The ophthalmic lens according to claim 1, wherein the continuous sine function is affected by a first hyperbolic tangent function, and the continuous cosine function is affected by a second hyperbolic tangent function.

5. The ophthalmic lens according to claim 4, wherein the sum of the first and second hyperbolic tangent functions is equal to one.

6. The ophthalmic lens according to claim 1, wherein the plurality of echelettes diffracts at least about 95% to a first diffractive order.

7. The ophthalmic lens according to claim 1, wherein the diffractive profile distributes light energy to the $0^{th}$ and $1^{st}$ diffractive orders in an amount that is greater than 95%.

8. The ophthalmic lens according to claim 1, wherein the continuous cosine function is defined by the equation:

$$v\Delta_{01}((C_1+C_2*\cos(\pi(\rho/q_1^2))))$$

wherein
v is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[1-[Y\text{min}+(Y\text{max}-Y\text{min})(C_3+C_4*\tan h(\sqrt{\rho}-X\_\text{shift})/\text{Width})+w)]]$$

wherein
Ymin is a parameter that affects the shape of the optical zone,
Ymax=$(2q_1^2-r_1^2)/(r_1^2-q_1^2)/r_1^2$,
$C_3$ is a variable,
$C_4$ is a variable,
$q_1$ is the size of an optical zone of a first or central echelette,
$r_1$ is a radius of a first or central echelette,
$(r_1-q_1)$ is the radial width of a transition zone,
X_shift=$q_1^2$,
Width is a parameter indicative of a width of a region blending the optical zone and the transition zone, and
w is a smoothing parameter.

9. The ophthalmic lens according to claim 1, wherein the continuous sine function is defined by the equation:

$$v\Delta_{01}((C_1+C_2*\sin(\pi(\rho-((r_1^2+q_1^2)/2)/(r_1^2-q_1^2))))$$

wherein
v is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[Y\text{min}+(Y\text{max}-Y\text{min})(C3+C4*\tan h(\sqrt{\rho}-X\_\text{shift})/\text{Width})+w)]$$

wherein
Ymin is a parameter that affects the shape of the optical zone,
Ymax=$(2q_1^2-r_1^2)/(r_1^2-q_1^2)/r_1^2$,
C3 is a variable,
C4 is a variable,
$q_1$ is the size of an optical zone of a first or central echelette,
$r_1$ is a radius of a first or central echelette,
$(r_1-q_1)$ is the radial width of a transition zone,
X_shift=$q_1^2$,
Width is a parameter indicative of a width of a region blending the optical zone and the transition zone, and
w is a smoothing parameter.

10. The ophthalmic lens according to claim 1, wherein the displacement function corresponds to a displacement from a reference plane perpendicular to the optical axis.

11. The ophthalmic lens according to claim 1, wherein the lens is a multifocal lens.

12. The ophthalmic lens according to claim 1, wherein the lens is a monofocal lens.

13. A method for treating an eye of a person, the method comprising:
administering a diffractive ophthalmic lens to the eye of the person, wherein the ophthalmic lens comprises an anterior face with an anterior refractive profile and a posterior face with a posterior refractive profile, the faces disposed about an optical axis, the lens further comprising a diffractive profile imposed on one of the refractive profiles, the diffractive profile comprising a plurality of echelettes, the diffractive profile characterized by a displacement function over the plurality of echelettes, the displacement function comprising the sum of a continuous cosine function and a continuous sine function over the plurality of echelettes, wherein the diffractive profile provides a light scatter characteristic that scatters less than 5% of light.

14. The method according to claim 13, wherein the continuous sine function is affected by a hyperbolic tangent function.

15. The method according to claim 13, wherein the continuous cosine function is affected by a hyperbolic tangent function.

16. The method according to claim 13, wherein the continuous sine function is affected by a first hyperbolic tangent function, and the continuous cosine function is affected by a second hyperbolic tangent function.

17. The method according to claim 16, wherein the sum of the first and second hyperbolic tangent functions is equal to one.

18. The method according to claim 13, wherein the plurality of echelettes diffracts at least about 95% to a first diffractive order.

19. The method according to claim 13, wherein the diffractive profile distributes light energy to the $0^{th}$ and $1^{st}$ diffractive orders in an amount that is greater than 95%.

20. The method according to claim 13, wherein the continuous cosine function is defined by the equation:

$$v\Delta_{01}((C_1+C_2*\cos(\pi(\rho/q_1^2))))$$

wherein
v is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[1-[Y\min+(Y\max-Y\min)(C_3+C_4*\tan h(\sqrt{\rho}-X\_shift)/Width)+w)]]$$

wherein
Ymin is a parameter that affects the shape of the optical zone,
$Y\max=(2q_1^2-r_1^2)/(r_1^2-q_1^2)/r_1^2$,
$C_3$ is a variable,
$C_4$ is a variable,
$q_1$ is the size of an optical zone of a first or central echelette,
$r_1$ is a radius of a first or central echelette,
$(r_1-q_1)$ is the radial width of a transition zone,
$X\_shift=q_1^2$,
Width is a parameter indicative of a width of a region blending the optical zone and the transition zone, and
w is a smoothing parameter.

21. The method according to claim 13, wherein the continuous sine function is defined by the equation:

$$v\Delta_{01}((C_1+C_2*\sin(\pi(\rho-((r_1^2+q_1^2)/2)/(r_1^2-q_1^2))))$$

wherein
v is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[Y\min+(Y\max-Y\min)(C3+C4*\tan h(\sqrt{\rho}-X\_shift)/Width)+w)]$$

wherein
Ymin is a parameter that affects the shape of the optical zone,
$Y\max=(2q_1^2-r_1^2)/(r_1^2-q_1^2)/r_1^2$,
C3 is a variable,
C4 is a variable,
$q_1$ is the size of an optical zone of a first or central echelette,
$r_1$ is a radius of a first or central echelette,
$(r_1-q_1)$ is the radial width of a transition zone,
$X\_shift=q_1^2$,
Width is a parameter indicative of a width of a region blending the optical zone and the transition zone, and
w is a smoothing parameter.

22. The method according to claim 13, wherein the displacement function corresponds to a displacement from a reference plane perpendicular to the optical axis.

23. The method according to claim 13, wherein the lens is a multifocal lens.

24. The method according to claim 13, wherein the lens is a monofocal lens.

25. A method of manufacturing an ophthalmic lens for an eye of a person, the method comprising:
obtaining a lens material; and
processing the lens material to produce the ophthalmic lens, so that the ophthalmic lens comprises an anterior face with an anterior refractive profile and a posterior face with a posterior refractive profile, the faces disposed about an optical axis, the lens further comprising a diffractive profile imposed on one of the refractive profiles, the diffractive profile comprising a plurality of echelettes, the diffractive profile characterized by a displacement function over the plurality of echelettes, the displacement function comprising the sum of a continuous cosine function and a continuous sine function over the plurality of echelettes, wherein the diffractive profile provides a light scatter characteristic that scatters less than 5% of light.

26. The method according to claim 25, wherein the continuous sine function is affected by a hyperbolic tangent function.

27. The method according to claim 25, wherein the continuous cosine function is affected by a hyperbolic tangent function.

28. The method according to claim 25, wherein the continuous sine function is affected by a first hyperbolic tangent function, and the continuous cosine function is affected by a second hyperbolic tangent function.

29. The method according to claim 28, wherein the sum of the first and second hyperbolic tangent functions is equal to one.

30. The method according to claim 25, wherein the plurality of echelettes diffracts at least about 95% to a first diffractive order.

31. The method according to claim 25, wherein the diffractive profile distributes light energy to the $0^{th}$ and $1^{st}$ diffractive orders in an amount that is greater than 95%.

32. The method according to claim 25, wherein the continuous cosine function is defined by the equation:

$$v\Delta_{01}((C_1+C_2*\cos(\pi(\rho/q_1^2))))$$

wherein
v is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and $q_1$ is the size of an optical zone of a first or central echelette, multiplied by the equation:

$$[1-[Y\text{min}+(Y\text{max}-Y\text{min})(C_3+C_4*\tan h(\sqrt{\rho}-X\_\text{shift})/\text{Width})+w)]]$$

wherein
Ymin is a parameter that affects the shape of the optical zone,
$Y\text{max}=(2q_1^2-r_1^2)/(r_1^2-q_1^2)/r_1^2$,
$C_3$ is a variable,
$C_4$ is a variable,
$q_1$ is the size of an optical zone of a first or central echelette,
$r_1$ is a radius of a first or central echelette,
$(r_1-q_1)$ is the radial width of a transition zone,
$X\_\text{shift}=q_1^2$,
Width is a parameter indicative of a width of a region blending the optical zone and the transition zone, and
w is a smoothing parameter.

33. The method according to claim 25, wherein the continuous sine function is defined by the equation:

$$v\Delta_{01}((C_1+C_2*\sin(\pi(\rho-((r_1^2+q_1^2)/2)/(r_1^2-q_1^2))))$$

wherein
$v$ is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[Y\text{min}+(Y\text{max}-Y\text{min})(C_3+C_4*\tan h(\sqrt{\rho}-X\_\text{shift})/\text{Width})+w)]$$

wherein
Ymin is a parameter that affects the shape of the optical zone,
$Y\text{max}=(2q_1^2-r_1^2)/(r_1^2-q_1^2)/r_1^2$,
C3 is a variable,
C4 is a variable,
$q_1$ is the size of an optical zone of a first or central echelette,
$r_1$ is a radius of a first or central echelette,
$(r_1-q_1)$ is the radial width of a transition zone,
$X\_\text{shift}=q_1^2$,
Width is a parameter indicative of a width of a region blending the optical zone and the transition zone, and
w is a smoothing parameter.

34. The method according to claim 25, wherein the displacement function corresponds to a displacement from a reference plane perpendicular to the optical axis.

35. The method according to claim 25, wherein the lens is a multifocal lens.

36. The method according to claim 25, wherein the lens is a monofocal lens.

37. An ophthalmic lens, comprising:
an anterior face with an anterior refractive profile and a posterior face with a posterior refractive profile, the faces disposed about an optical axis;
a diffractive profile imposed on one of the refractive profiles, the diffractive profile comprising a plurality of echelettes, the diffractive profile characterized by a displacement function over the plurality of echelettes, the displacement function comprising the sum of a continuous cosine function and a continuous sine function over the plurality of echelettes,
wherein the plurality of echelettes diffracts at least about 95% to a first diffractive order.

38. The ophthalmic lens according to claim 37, wherein the continuous sine function is affected by a hyperbolic tangent function.

39. The ophthalmic lens according to claim 37, wherein the continuous cosine function is affected by a hyperbolic tangent function.

40. The ophthalmic lens according to claim 37, wherein the continuous sine function is affected by a first hyperbolic tangent function, and the continuous cosine function is affected by a second hyperbolic tangent function.

41. The ophthalmic lens according to claim 40, wherein the sum of the first and second hyperbolic tangent functions is equal to one.

42. The ophthalmic lens according to claim 37, wherein the diffractive profile distributes light energy to the $0^{th}$ and $1^{st}$ diffractive orders in an amount that is greater than 95%.

43. The ophthalmic lens according to claim 37, wherein the continuous cosine function is defined by the equation:

$$v\Delta_{01}((C_1+C_2*\cos(\pi(\rho/q_1^2))))$$

wherein
$v$ is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
$\rho$ is square of the radius from the optical axis, and
$q_1$ is the size of an optical zone of a first or central echelette, multiplied by the equation:

$$[1-[Y\text{min}+(Y\text{max}-Y\text{min})(C_3+C_4*\tan h(\sqrt{\rho}-X\_\text{shift})/\text{Width})+w)]]$$

wherein
Ymin is a parameter that affects the shape of the optical zone,
$Y\text{max}=(2q_1^2-r_1^2)/(r_1^2-q_1^2)/r_1^2$,
$C_3$ is a variable,
$C_4$ is a variable,
$q_1$ is the size of an optical zone of a first or central echelette,
$r_1$ is a radius of a first or central echellete,
$(r_1-q_1)$ is the radial width of a transition zone,
$X\_\text{shift}=q_1^2$,
Width is a parameter indicative of a width of a region blending the optical zone and the transition zone, and
w is a smoothing parameter.

44. The ophthalmic lens according to claim 37, wherein the continuous sine function is defined by the equation:

$$v\Delta_{01}((C_1+C_2*\sin(\pi(\rho-((r_1^2+q_1^2)/2)/(r_1^2-q_1^2))))$$

wherein
$v$ is a variable,
$\Delta_{01}=(\lambda/(n_{iol}-n_{med}))*\alpha$,
$\lambda$ represents a design wavelength,
$\alpha=1.086*u$,
u is a variable,
$n_{iol}$ is the refractive index of the ophthalmic lens,
$n_{med}$ is the refractive index of the eye,
$C_1$ is a variable, $C_2$ is a variable,
ρ is square of the radius from the optical axis, and
$q_1$ is the size of an optical zone of a first or central echelette, multiplied by the equation:

$$[Y\text{min}+(Y\text{max}-Y\text{min})(C_3+C_4*\tan h(\sqrt{\rho}-X\_shift)/\text{Width})+w)]$$

wherein
Ymin is a parameter that affects the shape of the optical zone,
$Y\text{max}=(2q_1^2-r_1^2)/(r_1^2-q_1^2)/r_1^2$,
C3 is a variable,
C4 is a variable,
$q_1$ is the size of an optical zone of a first or central echelette,
$r_1$ is a radius of a first or central echelette,
$(r_1-q_1)$ is the radial width of a transition zone,
$X\_shift=q_1^2$,
Width is a parameter indicative of a width of a region blending the optical zone and the transition zone, and
w is a smoothing parameter.

45. The ophthalmic lens according to claim 37, wherein the displacement function corresponds to a displacement from a reference plane perpendicular to the optical axis.

46. The ophthalmic lens according to claim 37, wherein the lens is a multifocal lens.

47. The ophthalmic lens according to claim 37, wherein the lens is a monofocal lens.

48. An ophthalmic lens, comprising:
an anterior face with an anterior refractive profile and a posterior face with a posterior refractive profile, the faces disposed about an optical axis;
a diffractive profile imposed on one of the refractive profiles, the diffractive profile comprising a plurality of echelettes, the diffractive profile characterized by a displacement function over the plurality of echelettes, the displacement function comprising the sum of a continuous cosine function and a continuous sine function over the plurality of echelettes,
wherein the diffractive profile distributes light energy to the $0^{th}$ and $1^{st}$ diffractive orders in an amount that is greater than 95%.

49. The ophthalmic lens according to claim 48, wherein the continuous sine function is affected by a hyperbolic tangent function.

50. The ophthalmic lens according to claim 48, wherein the continuous cosine function is affected by a hyperbolic tangent function.

51. The ophthalmic lens according to claim 48, wherein the continuous sine function is affected by a first hyperbolic tangent function, and the continuous cosine function is affected by a second hyperbolic tangent function.

52. The ophthalmic lens according to claim 51, wherein the sum of the first and second hyperbolic tangent functions is equal to one.

53. The ophthalmic lens according to claim 48, wherein the continuous cosine function is defined by the equation:

$$v\Delta_{01}((C_1+C_2*\cos(\pi(\rho/q_1^2))))$$

wherein
v is a variable,
$\Delta_{01}=(\lambda/(n_{iol}-n_{med}))*\alpha$,
λ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
ρ is square of the radius from the optical axis, and
$q_1$ is the size of an optical zone of a first or central echelette, multiplied by the equation:

$$[1-[Y\text{min}+(Y\text{max}-Y\text{min})(C_3+C_4*\tan h(\sqrt{\rho}-X\_shift)/\text{Width})+w)]]$$

wherein
Ymin is a parameter that affects the shape of the optical zone,
$Y\text{max}=(2q_1^2-r_1^2)/(r_1^2-q_1^2)/r_1^2$,
$C_3$ is a variable,
$C_4$ is a variable,
$q_1$ is the size of an optical zone of a first or central echelette,
$r_1$ is a radius of a first or central echelette,
$(r_1-q_1)$ is the radial width of a transition zone,
$X\_shift=q_1^2$,
Width is a parameter indicative of a width of a region blending the optical zone and the transition zone, and
w is a smoothing parameter.

54. The ophthalmic lens according to claim 48, wherein the continuous sine function is defined by the equation:

$$v\Delta_{01}((C_1+C_2*\sin(\pi(\rho-((r_1^2+q_1^2)/2)/(r_1^2-q_1^2))))$$

wherein
v is a variable,
$\Delta_{01}=(\lambda/(n_{iol}-n_{med}))*\alpha$,
λ represents a design wavelength,
$\alpha=1.086*u$,
u is a variable,
$n_{iol}$ is the refractive index of the ophthalmic lens,
$n_{med}$ is the refractive index of the eye,
$C_1$ is a variable,
$C_2$ is a variable,
ρ is square of the radius from the optical axis, and
$q_1$ is the size of an optical zone of a first or central echelette, multiplied by the equation:

$$[Y\text{min}+(Y\text{max}-Y\text{min})(C_3+C_4*\tan h(\sqrt{\rho}-X\_shift)/\text{Width})+w)]$$

wherein
Ymin is a parameter that affects the shape of the optical zone,
$Y\text{max}=(2q_1^2-r_1^2)/(r_1^2-q_1^2)/r_1^2$,
C3 is a variable,
C4 is a variable,
$q_1$ is the size of an optical zone of a first or central echelette,
$r_1$ is a radius of a first or central echellete,
$(r_1-q_1)$ is the radial width of a transition zone,
$X\_shift=q_1^2$,
Width is a parameter indicative of a width of a region blending the optical zone and the transition zone, and
w is a smoothing parameter.

55. The ophthalmic lens according to claim 48, wherein the displacement function corresponds to a displacement from a reference plane perpendicular to the optical axis.

56. The ophthalmic lens according to claim 48, wherein the lens is a multifocal lens.

57. The ophthalmic lens according to claim 48, wherein the lens is a monofocal lens.

* * * * *